United States Patent
Lamont et al.

(10) Patent No.: US 10,914,745 B2
(45) Date of Patent: Feb. 9, 2021

(54) BIOMARKER-BASED METHODS FOR AIDING THE DIAGNOSIS OF STROKE

(71) Applicant: Randox Laboratories Ltd., Antrim (GB)

(72) Inventors: John Lamont, Antrim (GB); Ivan McConnell, Antrim (GB); Peter Fitzgerald, Antrim (GB)

(73) Assignee: Randox Laboratories Ltd.

( * ) Notice: Subject to any disclaimer, the term of this patent is extended or adjusted under 35 U.S.C. 154(b) by 401 days.

(21) Appl. No.: 15/457,297

(22) Filed: Mar. 13, 2017

(65) Prior Publication Data
US 2017/0184611 A1 Jun. 29, 2017

Related U.S. Application Data

(63) Continuation of application No. 14/361,880, filed as application No. PCT/GB2012/052993 on Dec. 3, 2012, now abandoned.

(30) Foreign Application Priority Data

Dec. 2, 2011 (GB) .................................. 1120781.8

(51) Int. Cl.
*G01N 33/68* (2006.01)
*C12Q 1/6883* (2018.01)

(52) U.S. Cl.
CPC ....... *G01N 33/6893* (2013.01); *C12Q 1/6883* (2013.01); *G01N 33/6842* (2013.01); *C12Q 2600/158* (2013.01); *G01N 2333/4737* (2013.01); *G01N 2333/5412* (2013.01); *G01N 2333/70503* (2013.01); *G01N 2333/70525* (2013.01); *G01N 2333/70542* (2013.01); *G01N 2333/70564* (2013.01); *G01N 2333/70578* (2013.01); *G01N 2333/7151* (2013.01); *G01N 2800/2871* (2013.01); *G01N 2800/32* (2013.01); *G01N 2800/60* (2013.01)

(58) Field of Classification Search
CPC ............... G01N 33/68; G01N 33/6893; G01N 33/70503
See application file for complete search history.

(56) References Cited

U.S. PATENT DOCUMENTS

| 5,474,796 A | 12/1995 | Brennan |
| 5,879,010 A | 3/1999 | Nilkanth et al. |
| 7,392,140 B2 | 6/2008 | Serena et al. |

FOREIGN PATENT DOCUMENTS

| EP | 1238284 A2 | 9/2002 | |
| WO | 0142793 | 6/2001 | |
| WO | 2002012892 A2 | 2/2002 | |
| WO | WO-2007124439 A2 * | 11/2007 | ......... G01N 33/6893 |
| WO | 2010012834 A1 | 2/2010 | |
| WO | 2010086697 A1 | 8/2010 | |

OTHER PUBLICATIONS

Elneihounn et al 1996. Stroke. 27: 1734-1738.*
C. G. Zimmermann-Ivol et al: "Fatty Acid Binding Protein as a Serum Marker for the Early Diagnosis of Stroke: A Pilot Study", Molecular & Cellular Proteomics, vol. 3, No. 1, Jan. 1, 2004 (Jan. 1, 2004), pp. 66-72, XP055076125.
International Preliminary Report on Patentability for Application No. PCT/GB2012/052993 dated Jun. 12, 2014.
International Search Report and Written Opinion for Application No. PCT/GB2012/052993 dated Sep. 3, 2013.
Ng et al., "Biomedical applications of protein chips", J. Cell Mol. Med. vol. 6, No. 3, Jul. 23, 2002, pp. 329-340.
Simundic Ana-Maria et al: "Soluble adhesion molecules in acute ischemic stroke.", Clinical and Investigative Medicine. Medecine Clinique Et Experimentale Apr. 2004, vol. 27, No. 2, Apr. 2004 (Apr. 2004), pp. 86-92.
Tuttolomondo A et al: "Immuno-inflammatory and thromboticifibrinolytic variables associated with acute ischemic stroke diagnosis", Atherosclerosis, Elsevier Ireland Ltd, IE, vol. 203, No. 2, Apr. 1, 2009 (Apr. 1, 2009), pp. 503-508, XP026032005.
Tuttolomondo A et al: "Inmune-inflammatory markers and arterial stiffness indexes in subjects with acute ischemic stroke", Atherosclerosis, Elsevier Ireland Ltd, IE, vol. 213, No. 1, Nov. 1, 2010 (Nov. 1, 2010), pp. 311-318, XP027437603.
Wunderlich M T et al: "Release of brain-type and heart-type fatty acid-binding proteins in serum after acute ischaemic stroke", Journal of Neurology, Steinkopff-Verlag, DA, vol. 252, No. 6, Jun. 1, 2005 (Jun. 1, 2005), pp. 718-724, XP019342470.

* cited by examiner

*Primary Examiner* — Zachary C Howard
(74) *Attorney, Agent, or Firm* — Lerner, David, Littenberg, Krumholz & Mentlik, LLP

(57) ABSTRACT

The present invention provides biomarker-based methods for diagnosing stroke in a patient suspected of having suffered a stroke, and also for discriminating between ischemic stroke and transient ischemic attack. Substrates comprising probes for specific combinations of biomarkers useful in the methods of the invention are also described.

1 Claim, 12 Drawing Sheets

BIOMARKER-BASED METHODS FOR AIDING THE DIAGNOSIS OF STROKE

CROSS-REFERENCE TO RELATED APPLICATIONS

The present application is a continuation of U.S. patent application Ser. No. 14/361,880, filed on May 30, 2014, which application is a national phase entry under 35 U.S.C. § 371 of International Application No. PCT/GB2012/052993, filed Dec. 3, 2012, published as WO 2013/079981, which claims priority to Great Britain Patent Application No. GB 1120781.8, filed Dec. 2, 2011, the disclosures of which are incorporated herein by reference.

BACKGROUND TO THE INVENTION

Stroke is the third leading cause of death worldwide and can be defined as the rapidly developing loss of brain function(s) due to interruption in the blood supply to the brain. According to the World Health Organisation, 15 million people per year suffer stroke worldwide, with 5 million dying and a further 5 million being permanently disabled. High blood pressure is estimated to be a contributing factor in 12.7 million of these 15 million stroke cases. In the UK, approximately 150,000 people have a stroke each year and stroke accounts for around 53,000 deaths per year. Stroke costs the economy an estimated .English Pound.8 billion per year in England alone and stroke patients occupy approximately 20 percent of all acute hospital beds and 25 percent of long term beds. Stroke can be classified into three subtypes:

i) ischaemic stroke (IS) occurs when blood supply to the brain is decreased, resulting in brain damage. An ischemic stroke occurs when a blood vessel becomes blocked, usually via a blood clot. This clot may form locally at an atherosclerotic plaque (thrombotic stroke) or alternatively may occur due to a travelling particle or debris that has originated from elsewhere in the bloodstream (embolic stroke);

ii) transient ischaemic attack (TIA) is a 'mini stroke' that occurs when blood supply to the brain is temporarily decreased. A TIA is diagnosed if symptoms are quickly resolved (within 24 hours with the individual returning to normal health); and iii) haemorrhagic stroke (HS) occurs when blood accumulates within the skull vault, usually when a weakened blood vessel ruptures. Haemorrhagic stroke can be classified into two major subtypes, namely intracerebral (within the brain tissue) and subarachnoid (around the surface of the brain and under its protective layer).

IS and TIA account for approximately 85% of all stroke cases and HS accounts for 15%. In order to minimise neurological damage following stroke it is crucial that stroke patients are rapidly and accurately diagnosed, so that appropriate treatment can be administered. For example, in order to break down clots thrombolytic therapy such as tissue plasminogen activator (TPA) can be administered. However, such therapy is only warranted in IS and is detrimental in HS. The nature of TIA does not require such therapy and blood thinners such as warfarin and aspirin are prescribed in such cases.

At present, if stroke is suspected, physical symptoms are evaluated and a computerised tomography (CT) scan is usually performed. A CT scan has good sensitivity for identifying HS patients (approximately 90% sensitivity) but poor sensitivity for identifying IS and TIA patients (approximately 20% sensitivity). In practice minimal or no tissue damage occurs for TIA due to its transient nature, therefore CT scanning is ineffective as a diagnostic technique. Magnetic Resonance Imaging (MRI) has improved sensitivity for IS diagnosis (up to approximately 80%) but increased time requirements, machine accessibility, and high cost have limited its use for stroke diagnosis. The poor sensitivity of CT scanning for the detection of IS and TIA means that a biological fluid-based diagnostic biomarker tests for detecting IS and TIA would be an invaluable tool to aid clinicians in the diagnosis of stroke sub-type. Biological fluid-based biomarkers have the potential to expedite and increase the accuracy of stroke diagnosis.

Various candidate biomarkers have been proposed for the diagnosis of stroke and stroke sub-type delineation and there are several descriptions of IS/TIA versus HS discrimination in the prior art, for example EP1238284, WO 2010/086697, WO 2010/012834, and WO 2002/012892.

EP1419388 discloses data that distinguishes IS from HS and all stroke types from non-stroke controls. However, none have thus far found use in clinical practice and there is a real clinical need for biomarkers of all three stroke sub-types that have high sensitivity and specificity to enable accurate diagnosis.

Furthermore, there are currently no biomarkers for delineating IS from TIA. The delineation of IS from TIA using a blood test would facilitate a more informed clinical decision, potentially render unnecessary expensive and less expeditious neuroimaging diagnostics, and would improve the identification of patients who may be in need of thrombolytic therapeutic intervention.

SUMMARY OF THE INVENTION

According to a first aspect, the present invention provides a method for diagnosing stroke in a patient suspected of having a stroke, comprising determining the concentration of at least two biomarkers in an in vitro sample obtained from the patient and establishing the significance of the concentration of the biomarkers by comparing the concentration value for each biomarker with a corresponding control value, wherein the at least two biomarkers are selected from ICAM-1, L-selectin, P-selectin, VCAM-1, IL-6, sTNFR1, D-dimer and CRP, and wherein at least one of the two biomarkers is selected from ICAM-1, L-selectin, P-selectin and VCAM-1.

According to a second aspect, the present invention provides a substrate comprising probes for at least two biomarkers selected from ICAM-1, L-selectin, P-selectin, VCAM-1, IL-6, sTNFR1, D-dimer and CRP for use in a method according to the first aspect of the invention, wherein the substrate comprises a probe for at least one of ICAM-1, L-selectin, P-selectin and VCAM-1.

According to a third aspect, the invention is directed to the use of a substrate according to the second aspect in a method for diagnosing stroke according to the first aspect.

According to a fourth aspect, the present prevention provides a method of aiding the diagnosis of ischaemic stroke in a patient suspected of having a stroke, comprising
i) determining the concentration of VCAM-1 and one or more biomarkers selected from h-FABP, IL-6 and CRP in an in vitro sample obtained from the patient; and ii) establishing the significance of the concentration of the biomarkers by comparing the concentration value for each biomarker with a corresponding control value, wherein the corresponding control value is the concentration value for the corresponding biomarker determined from an in vitro sample obtained from a transient ischaemic attack patient or patients. This method can be used to differentially diagnose between ischemic stroke and a transient ischaemic attack.

According to a fifth aspect, the present invention provides a substrate comprising probes for VCAM-1 and at least one other biomarker selected from h-FABP, IL-6 and CRP for use in a method according to the fourth aspect of the invention.

According to a sixth aspect, the invention is directed to the use of a substrate according to the fifth aspect in a method for diagnosing stroke according to the fourth aspect.

DETAILED DESCRIPTION OF THE INVENTION

Figure 1:
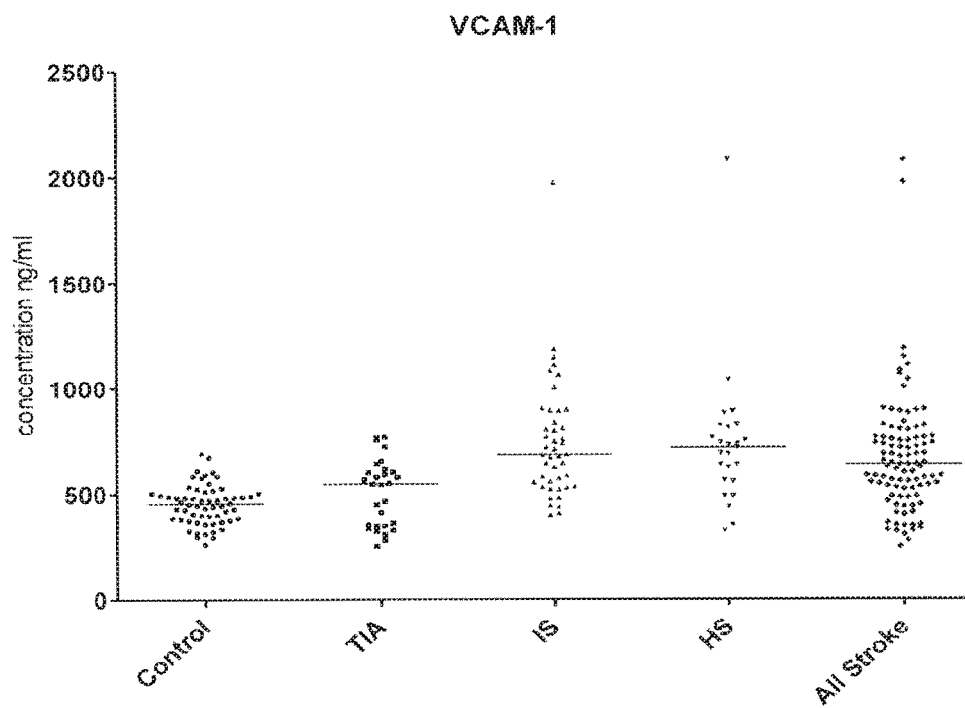
FIG. 1 is a graph showing the concentration of VCAM-1 for all stroke patients, each stroke sub-type and the control subjects.

The present invention relates to biomarker-based methods and biochips that can be used for rapid diagnosis of stroke, and furthermore to aid discrimination between the three stroke sub-types: haemorrhagic stroke (HS), ischemic stroke (IS) and transient ischemic attack (TIA).

Unless stated otherwise, all references herein to the term 'stroke' encompasses all three forms of stroke.

References herein to 'a patient suspected of having a stroke' or 'having had a stroke' include a patient who is suspected of currently suffering from a stroke or who is suspected of having previously had a stroke. The stroke may have been a recent event, such an event having initiated the process of the individual seeking clinical help.

The terms "subject" and "patient" may be used interchangeably herein and refer to a mammal including a non-primate (e.g. a cow, pig, horse, dog, cat, rat and mouse) and a primate (e.g. a monkey and human). Preferably the subject or patient is a human.

As used herein, the term 'biomarker' refers to a molecule present in a biological sample obtained from a patient, the concentration of which in said sample may be indicative of a pathological state. Various biomarkers that have been found to be useful in diagnosing stroke and stroke sub-types, either alone or in combination with other diagnostic methods, or as complementary biomarkers in combination with other biomarkers, are described herein. A used herein, the term 'complementary biomarker' refers to a biomarker that can be used in conjunction with other stroke biomarkers to support diagnosis.

It is well understood in the art that biomarker normal or 'background' concentrations may exhibit slight variation due to, for example, age, gender or ethnic/geographical genotypes. As a result, the cut-off value used in the methods of the invention may also slightly vary due to optimization depending upon the target patient/population.

The biological sample obtained from a patient is preferably a blood, serum or plasma sample. As used herein, the term 'in vitro' has its usual meaning in the art and refers to a sample that has been removed from a patient's body.

When a blood sample is taken from the patient for analysis, whole blood, serum or plasma is analysed. Analysis of the blood sample can be by way of several analytical methodologies such as mass spectrometry linked to a pre-separation step such as chromatography. The preferred methodology is based on immuno-detection Immuno-detection technology is also readily incorporated into transportable or hand-held devices for use outside of the clinical environment. A quantitative immunoassay such as a Western blot or ELISA can be used to detect the amount of protein. A preferred method of analysis comprises using a multi-analyte biochip which enables several proteins to be detected and quantified simultaneously. 2D Gel Electrophoresis is also a technique that can be used for multi-analyte analysis.

A first aspect of the invention provides a method for diagnosing stroke in a patient suspected of having a stroke, comprising determining the concentration of at least two biomarkers in an in vitro sample obtained from the patient and establishing the significance of the concentration of the biomarkers by comparing the concentration value for each biomarker with a corresponding control value, wherein the at least two biomarkers are selected from ICAM-1, L-selectin, P-selectin, VCAM-1, IL-6, sTNFR1, D-dimer and CRP, and wherein at least one of the two biomarkers is selected from ICAM-1, L-selectin, P-selectin and VCAM-1.

Preferably the at least two biomarkers are selected from (i) ICAM-1 or VCAM-1 and (ii) L-selectin or P-selectin, and more preferably they are ICAM-1 and L-selectin. Combinations of three or more biomarkers are also preferred as they show the highest sensitivity and specificity.

In preferred embodiments, the method further comprises determining the sample concentration of one or more biomarkers selected from IL-6, sTNFR1, D-dimer and CRP. The method may also further comprise determining the sample concentration of h-FABP.

For the avoidance of doubt, in the context of this aspect of the invention, 'stroke' refers to 'all stroke' (i.e. all three stroke sub-types).

Preferred biomarker combinations are those listed in Table 1 or Table 2. These tables provide sensitivity, specificity and AUC data for different biomarker combinations for stoke v control.

TABLE 1

| Biomarker(s) | % Sensitivity | % Specificity | AUC |
|---|---|---|---|
| 1. VCAM-1 ICAM-1 | 80.6 | 75.0 | 0.831 |
| 2. VCAM-1 Psel | 87.8 | 71.7 | 0.913 |
| 3. VCAM-1 Lsel | 89.8 | 86.7 | 0.943 |
| 4. VCAM-1 IL-6 | 80.6 | 78.3 | 0.879 |
| 5. VCAM-1 CRP | 78.6 | 75.0 | 0.826 |
| 6. VCAM-1 D-dimer | 87.8 | 76.7 | 0.686 |
| 7. VCAM-1 NGAL | 81.6 | 73.3 | 0.867 |
| 8. VCAM-1 sTNFRI | 82.7 | 75.0 | 0.832 |
| 9. IL-6 sTNFRI | 78.6 | 75.0 | 0.870 |
| 10. ICAM-1 Psel | 92.9 | 76.7 | 0.932 |
| 11. ICAM-1 Lsel | 90.8 | 90.0 | 0.954 |
| 12. ICAM-1 IL-6 | 83.7 | 83.3 | 0.897 |
| 13. ICAM-1 CRP | 79.6 | 80.0 | 0.822 |
| 14. ICAM-1 D-dimer | 86.7 | 76.7 | 0.905 |
| 15. ICAM-1 NGAL | 81.6 | 73.3 | 0.836 |
| 16. ICAM-1 sTNFRI | 77.6 | 73.3 | 0.832 |
| 17. IL-6 NGAL | 87.8 | 81.7 | 0.909 |
| 18. Psel Lsel | 88.8 | 65.0 | 0.867 |
| 19. Psel IL-6 | 90.8 | 78.3 | 0.937 |
| 20. Psel CRP | 87.8 | 68.3 | 0.888 |
| 21. Psel D-dimer | 90.6 | 85.0 | 0.931 |
| 22. Psel NGAL | 86.7 | 58.3 | 0.838 |
| 23. Psel sTNFRI | 86.7 | 65.0 | 0.685 |
| 24. IL-6 D-dimer | 64.7 | 81.7 | 0.910 |
| 25. Lsel IL-6 | 84.7 | 85.0 | 0.907 |
| 26. Lsel CRP | 86.7 | 71.7 | 0.863 |
| 27. Lsel D-dimer | 68.8 | 80.0 | 0.894 |
| 28. Lsel NGAL | 90.8 | 51.7 | 0.833 |
| 29. Lsel sTNFRI | 84.7 | 61.7 | 0.862 |
| 30. IL-6 CRP | 76.5 | 81.7 | 0.870 |
| 31. IL-6 NGAL sTNFRI | 89.8 | 81.7 | 0.942 |
| 32. IL-6 D-dimer sTFNRI | 85.7 | 80.0 | 0.908 |
| 33. IL-6 D-dimer NGAL | 92.9 | 83.3 | 0.943 |
| 34. IL-6 CRP sTNFRI | 75.5 | 78.3 | 0.872 |
| 35. VCAM-1 ICAM-1 Psel | 91.8 | 80.0 | 0.946 |
| 36. VCAM-1 ICAM-1 Lsel | 93.9 | 93.3 | 0.975 |
| 37. VCAM-1 ICAM-1 IL-6 | 85.7 | 81.7 | 0.906 |
| 38. VCAM-1 ICAM-1 CRP | 80.6 | 78.3 | 0.853 |
| 39. VCAM-1 ICAM-1 D-dimer | 88.8 | 80.0 | 0.907 |
| 40. VCAM-1 ICAM-1 NGAL | 85.7 | 80.0 | 0.895 |
| 41. VCAM-1 ICAM-1 sTNFRI | 82.7 | 75.0 | 0.856 |
| 42. IL-6 CRP NGAL | 85.7 | 80.0 | 0.915 |
| 43. VCAM-1 Psel Lsel | 92.9 | 88.3 | 0.957 |
| 44. VCAM-1 Psel IL-6 | 90.8 | 76.7 | 0.962 |
| 45. VCAM-1 Psel CRP | 87.8 | 78.3 | 0.930 |
| 46. VCAM-1 Psel D-dimer | 89.8 | 83.3 | 0.955 |
| 47. VCAM-1 Psel NGAL | 89.8 | 76.7 | 0.932 |
| 48. VCAM-1 Psel sTNFRI | 88.8 | 76.7 | 0.923 |
| 49. IL-6 CRP D-dimer | 81.6 | 80.0 | 0.911 |
| 50. VCAM-1 Lsel IL-6 | 89.8 | 90.0 | 0.957 |
| 51. VCAM-1 Lsel CRP | 91.8 | 91.7 | 0.951 |

TABLE 1-continued

| Biomarker(s) | % Sensitivity | % Specificity | AUC |
|---|---|---|---|
| 52. VCAM-1 Lsel D-dimer | 89.8 | 85.0 | 0.946 |
| 53. VCAM-1 Lsel NGAL | 92.9 | 83.3 | 0.962 |
| 54. VCAM-1 Lsel sTNRI | 83.3 | 87.8 | 0.947 |
| 55. Lsel NGAL sTNFRI | 89.8 | 80.0 | 0.931 |
| 56. VCAM-1 IL-6 CRP | 79.6 | 81.7 | 0.881 |
| 57. VCAM-1 IL-6 D-dimer | 86.7 | 88.3 | 0.916 |
| 58. VCAM-1 IL-6 NGAL | 91.8 | 86.7 | 0.941 |
| 59. VCAM-1 IL-6 sTNFRI | 81.6 | 80.0 | 0.882 |
| 60. Lsel D-dimer sTNFRI | 83.7 | 76.7 | 0.905 |
| 61. VCAM-1 CRP D-dimer | 85.7 | 81.7 | 0.895 |
| 62. VCAM-1 CRP NGAL | 87.8 | 81.7 | 0.911 |
| 63. VCAM-1 CRP sTNFRI | 80.6 | 78.3 | 0.837 |
| 64. Lsel D-dimer NGAL | 91.8 | 85.0 | 0.921 |
| 65. VCAM-1 D-dimer NGAL | 90.8 | 96.7 | 0.938 |
| 66. VCAM-1 D-dimer sTNFRI | 87.8 | 80.0 | 0.891 |
| 67. Lsel CRP sTNFRI | 84.7 | 73.3 | 0.875 |
| 68. VCAM-1 NGAL sTNFRI | 89.8 | 80.0 | 0.930 |
| 69. Lsel CRP D-dimer | 86.7 | 76.7 | 0.908 |
| 70. Lsel CRP NGAL | 86.7 | 73.3 | 0.882 |
| 71. ICAM-1 Psel Lsel | 95.9 | 91.7 | 0.977 |
| 72. ICAM-1 Psel IL-6 | 93.9 | 91.7 | 0.979 |
| 73. ICAM-1 Psel CRP | 92.9 | 83.3 | 0.949 |
| 74. ICAM-1 Psel D-dimer | 93.9 | 88.3 | 0.969 |
| 75. ICAM-1 Psel NGAL | 88.8 | 78.3 | 0.938 |
| 76. ICAM-1 Psel sTNFRI | 91.8 | 81.7 | 0.946 |
| 77. Lsel IL-6 sTNFRI | 84.7 | 81.7 | 0.911 |
| 78. ICAM-1 Lsel IL-6 | 92.9 | 90.0 | 0.975 |
| 79. ICAM-1 Lsel CRP | 89.8 | 90.0 | 0.958 |
| 80. ICAM-1 Lsel D-dimer | 90.8 | 88.3 | 0.964 |
| 81. ICAM-1 Lsel NGAL | 91.8 | 86.7 | 0.963 |
| 82. ICAM-1 Lsel sTNFRI | 91.8 | 88.3 | 0.965 |
| 83. Lsel IL-6 NGAL | 90.8 | 83.3 | 0.920 |
| 84. ICAM-1 IL-6 CRP | 8.7 | 83.3 | 0.896 |
| 85. ICAM-1 IL-6 D-dimer | 87.8 | 85.0 | 0.931 |
| 86. ICAM-1 IL-6 NGAL | 89.6 | 86.7 | 0.934 |
| 87. ICAM-1 IL-6 sTNFRI | 84.7 | 80.0 | 0.903 |
| 88. Lsel IL-6 D-dimer | 86.7 | 81.7 | 0.920 |
| 89. ICAM-1 CRP D-dimer | 88.0 | 85.0 | 0.911 |
| 90. ICAM-1 CRP NGAL | 85.7 | 76.7 | 0.682 |
| 91. ICAM-1 CRP sTNFRI | 77.6 | 73.3 | 0.844 |
| 92. Lsel IL-6 CRP | 87.8 | 81.7 | 0.914 |
| 93. ICAM-1 D-dimer NGAL | 90.6 | 63.3 | 0.932 |
| 94. ICAM-1 D-dimer sTNFRI | 87.8 | 80.0 | 0.909 |
| 95. Psel NGAL sTNFRI | 89.8 | 76.7 | 0.930 |
| 96. ICAM-1 NGAL sTNFRI | 87.8 | 83.3 | 0.920 |
| 97. ICAM-1 NGAL sTNFRI | 87.8 | 83.3 | 0.920 |
| 98. Psel D-dimer sTNFRI | 89.8 | 81.7 | 0.930 |
| 99. Psel D-dimer NGAL | 91.8 | 86.7 | 0.947 |
| 100. Psel Lsel IL-6 | 89.8 | 78.3 | 0.943 |
| 101. Psel Lsel CRP | 89.8 | 75.0 | 0.903 |
| 102. Psel Lsel D-dimer | 90.8 | 83.3 | 0.936 |
| 103. Psel Lsel NGAL | 88.8 | 70.0 | 0.873 |
| 104. Psel Lsel sTNFRI | 90.8 | 71.7 | 0.914 |
| 105. Psel CRP sTNFRI | 87.6 | 70.0 | 0.897 |
| 106. Psel IL-6 CRP | 88.8 | 76.7 | 0.945 |
| 107. Psel IL-6 D-dimer | 90.8 | 88.3 | 0.957 |
| 108. Psel IL-6 NGAL | 92.9 | 88.3 | 0.953 |
| 109. Psel IL-6 sTNDRI | 89.6 | 78.3 | 0.944 |
| 110. Psel CRP NGAL | 86.7 | 75.0 | 0.907 |
| 111. Psel CRP D-dimer | 91.8 | 85.0 | 0.946 |
| 112. VCAM-1 IL-6, NGAL sTNFRI | 91.8 | 90.0 | 0.961 |
| 113. VCAM-1 D-dimer, NGAL sTNFRI | 89.8 | 88.3 | 0.959 |
| 114. ICAM-1, Lsel IL-6 D-dimer | 92.9 | 90.0 | 0.980 |
| 115. ICAM-1 Lsel IL-6 NGAL | 94.9 | 91.7 | 0.983 |
| 116. ICAM-1 Lsel IL-6 sTNFRI | 92.9 | 91.7 | 0.978 |
| 117. ICAM-1 Lsel D-dimer NGAL | 94.9 | 91.7 | 0.975 |
| 118. ICAM-1 Lsel D-dimer sTNFRI | 93.9 | 90.0 | 0.975 |
| 119. ICAM-1 Lsel NGAL sTNFRI | 96.9 | 95.0 | 0.978 |
| 120. ICAM-1 IL-6 D-dimer NGAL | 91.8 | 88.3 | 0.966 |
| 121. ICAM-1 IL-6 D-dimer sTNFRI | 86.7 | 86.7 | 0.932 |
| 122. ICAM-1 IL-6 NGAL sTNFRI | 92.9 | 85.0 | 0.967 |
| 123. ICAM-1 D-dimer NGAL sTNFRI | 91.8 | 85.0 | 0.959 |
| 124. Lsel IL-6 D-dimer NGAL | 92.9 | 88.3 | 0.948 |
| 125. Psel Lsel IL-6 ICAM-1 | 95.9 | 95.0 | 0.995 |
| 126. Lsel IL-6 NGAL sTNFRI | 93.9 | 85.0 | 0.958 |
| 127. Lsel D-dimer NGAL sTNFRI | 90.8 | 86.7 | 0.946 |
| 128. VCAM-1 ICAM-1 Lsel IL-6 | 96.9 | 95.0 | 0.985 |
| 129. VCAM-1 ICAM-1 Lsel D-dimer | 94.9 | 93.3 | 0.978 |

TABLE 1-continued

| Biomarker(s) | % Sensitivity | % Specificity | AUC |
|---|---|---|---|
| 130. VCAM-1 ICAM-1 Lsel NGAL | 96.9 | 93.3 | 0.94 |
| 131. VCAM-1 ICAM-1 Lsel sTNFRI | 94.9 | 95.0 | 0.977 |
| 132. VCAM-1 ICAM-1 IL-6 D-dimer | 86.7 | 86.7 | 0.933 |
| 133. VCAM-1 ICAM-1 IL-6 NGAL | 91.8 | 83.3 | 0.954 |
| 134. Psel Lsel IL-6 VCAM-1 | 93.9 | 86.7 | 0.972 |
| 135. VCAM-1 ICAM-1 D-dimer NGAL | 89.8 | 80.0 | 0.948 |
| 136. Psel Lsel IL-6 D-dimer | 89.8 | 88.3 | 0.959 |
| 137. VCAM-1 ICAM-1 NGAL sTNRI | 85.7 | 81.7 | 0.944 |
| 138. VCAM-1 Lsel IL-6 D-dimer | 90.8 | 91.7 | 0.956 |
| 139. VCAM-1 Lsel IL-6 NGAL | 92.9 | 91.7 | 0.972 |
| 140. VCAM-1 Lsel IL-6 sTNFRI | 88.8 | 90.0 | 0.959 |
| 141. VCAM-1 Lsel D-dimer NGAL | 93.9 | 90.0 | 0.968 |
| 142. VCAM-1 Lsel D-dimer sTNFRI | 92.9 | 88.3 | 0.949 |
| 143. VCAM-1 Lsel NGAL sTNFRI | 91.8 | 90.0 | 0.970 |
| 144. VCAM-1 IL-6 D-dimer NGAL | 92.9 | 88.3 | 0.971 |
| 145. IL-6 D-dimer NGAL sTNFRI | 89.8 | 88.3 | 0.971 |
| 146. Psel Lsel IL-6 NGAL | 93.9 | 85.0 | 0.953 |
| 147. CRP D-dimer ICAM-1 IL-6 | 87.8 | 85.0 | 0.932 |
| 148. CRP D-dimer ICAM-1 Lsel | 91.8 | 91.7 | 0.966 |
| 149. CRP D-dimer ICAM-1 NGAL | 87.8 | 83.3 | 0.939 |
| 150. Psel Lsel ICAM-1 D-dimer | 98.0 | 93.3 | 0.989 |
| 151. Psel Lsel ICAM-1 CRP | 95.9 | 90.0 | 0.980 |
| 152. Psel IL-6 ICAM-1 D-dimer | 95.9 | 93.3 | 0.988 |
| 153. CRP D-dimer IL-6 NGAL | 91.8 | 85.0 | 0.948 |
| 154. CRP Lsel sTNFRI VCAM-1 | 87.8 | 90.0 | 0.952 |
| 155. Psel IL-6 ICAM-1 NGAL | 94.9 | 90.0 | 0.983 |
| 156. CRP D-dimer Lsel NGAL | 93.9 | 80.0 | 0.935 |
| 157. CRP Lsel NGAL sTNFRI | 91.8 | 81.7 | 0.933 |
| 158. CRP D-dimer Lsel VCAM-1 | 88.3 | 91.8 | 0.950 |
| 159. Lsel Psel VCAM-1 ICAM-1 | 94.9 | 95.0 | 0.986 |
| 160. CRP D-dimer NGAL VCAM-1 | 90.8 | 85.0 | 0.950 |
| 161. CRP IL-6 NGAL VCAM-1 | 90.8 | 88.3 | 0.947 |
| 162. CRP ICAM-1 IL-6 Lsel | 92.9 | 90.0 | 0.975 |
| 163. CRP ICAM-1 IL-6 NGAL | 88.8 | 83.3 | 0.938 |
| 164. CRP IL-6 NGAL sTNFRI | 89.8 | 80.0 | 0.947 |
| 165. CRP IL-6 Lsel VCAM-1 | 90.6 | 91.7 | 0.957 |
| 166. CRP ICAM-1 Lsel NGAL | 94.9 | 88.3 | 0.970 |
| 167. CRP ICAM-1 Lsel sTNFRI | 91.8 | 88.3 | 0.968 |
| 168. CRP ICAM-1 Lsel VCAM-1 | 93.9 | 95.0 | 0.976 |
| 169. CRP IL-6 Lsel NGAL | 88.8 | 83.3 | 0.931 |
| 170. CRP NGAL sTNFRI VCAM-1 | 87.8 | 85.0 | 0.934 |

TABLE 2

| Biomarkers | % Sensitivity | % Specificity | AUC |
|---|---|---|---|
| 1. VCAM1 + FABP | 89.8 | 95.0 | 0.960 |
| 2. ICAM1 + FABP | 92.9 | 93.3 | 0.964 |
| 3. PSel + FABP | 95.9 | 91.7 | 0.961 |
| 4. LSel + FABP | 91.8 | 95.0 | 0.970 |
| 5. VCAM1 + ICAM1 + FABP | 92.9 | 93.3 | 0.965 |
| 6. VCAM1 + PSel + FABP | 95.9 | 91.7 | 0.983 |
| 7. VCAM1 + Lsel + FABP | 92.9 | 96.7 | 0.971 |
| 8. VCAM1 + IL6 + FABP | 90.8 | 95.0 | 0.961 |
| 9. VCAM1 + CRP + FABP | 89.8 | 95.0 | 0.960 |
| 10. VCAM1 + DDimer + FABP | 90.8 | 95.0 | 0.963 |
| 11. VCAM1 + NGAL + FABP | 98.0 | 93.3 | 0.986 |
| 12. VCAM1 + sTNFRI + FABP | 89.8 | 91.7 | 0.962 |
| 13. ICAM1 + PSel + FABP | 96.9 | 93.3 | 0.990 |
| 14. ICAM1 + LSel + FABP | 96.9 | 93.3 | 0.993 |
| 15. ICAM1 + IL6 + FABP | 91.8 | 91.7 | 0.966 |
| 16. ICAM1 + CRP + FABP | 92.9 | 93.3 | 0.964 |
| 17. ICAM1 + DDimer + FABP | 92.9 | 95.0 | 0.968 |
| 18. ICAM1 + NGAL + FABP | 96.9 | 95.0 | 0.984 |
| 19. ICAM1 + sTNFRI + FABP | 91.8 | 93.3 | 0.966 |
| 20. PSel + LSel + FABP | 95.9 | 93.3 | 0.985 |
| 21. PSel + IL6 + FABP | 93.9 | 93.3 | 0.985 |
| 22. PSel + CRP + FABP | 92.9 | 91.7 | 0.983 |
| 23. PSel + DDimer + FABP | 93.9 | 93.3 | 0.964 |
| 24. PSel + NGAL + FABP | 96.9 | 96.7 | 0.993 |
| 25. PSel + sTNFRI + FABP | 93.9 | 91.7 | 0.983 |
| 26. Lsel + IL6 + FABP | 90.8 | 93.3 | 0.975 |
| 27. LSel + CRP + FABP | 91.8 | 93.3 | 0.970 |
| 28. IL6 + CRP + FABP | 91.8 | 96.7 | 0.962 |
| 29. IL6 + DDimer + FABP | 89.8 | 93.3 | 0.963 |
| 30. IL6 + NGAL + FABP | 91.8 | 93.3 | 0.990 |
| 31. IL6 + sTNFRI + FABP | 89.8 | 91.7 | 0.963 |
| 32. LSel + DDimer + FABP | 90.8 | 93.3 | 0.973 |
| 33. LSel + NGAL + FABP | 95.9 | 93.3 | 0.989 |
| 34. LSel + sTNFRI + FABP | 92.9 | 93.3 | 0.972 |
| 35. FABP + CRP + DDimer | 90.8 | 93.3 | 0.962 |
| 36. FABP + CRP + NGAL | 95.9 | 93.3 | 0.985 |
| 37. FABP + CRP + sTNFRI | 90.8 | 93.3 | 0.959 |
| 38. FABP + DDimer + NGAL | 95.9 | 93.3 | 0.985 |
| 39. FABP + DDimer + sTNFRI | 91.8 | 93.3 | 0.962 |
| 40. CRP + IL6 + FABP | 89.8 | 93.3 | 0.962 |
| 41. DDimer + IL6 + FABP | 91.8 | 93.3 | 0.963 |
| 42. NGAL + IL6 + FABP | 95.9 | 93.3 | 0.990 |
| 43. sTNFRI + IL6 + FABP | 89.8 | 91.7 | 0.963 |
| 44. IL6 + NGAL + FABP + DDimer | 96.9 | 93.3 | 0.990 |
| 45. LSel + NGAL + FABP + DDimer | 95.9 | 93.3 | 0.992 |
| 46. LSel + NGAL + FABP + IL6 | 94.9 | 93.3 | 0.994 |
| 47. PSel + sTNFRI + FABP + DDimer | 93.9 | 93.3 | 0.985 |
| 48. PSel + sTNFRI + FABP + NGAL | 96.9 | 96.7 | 0.994 |
| 49. PSel + IL6 + FABP + DDimer | 93.9 | 91.7 | 0.986 |
| 50. PSel + IL6 + FABP + NGAL | 96.9 | 95.0 | 0.996 |
| 51. PSel + LSel + FABP + DDimer | 95.9 | 93.3 | 0.987 |
| 52. PSel + LSel + FABP + IL6 | 93.9 | 91.7 | 0.987 |
| 53. PSel + LSel + FABP + NGAL | 96.9 | 96.7 | 0.994 |
| 54. PSel + LSel + FABP + CRP | 94.9 | 93.3 | 0.985 |
| 55. ICAM1 + NGAL + FABP + IL6 | 95.9 | 93.3 | 0.991 |
| 56. ICAM1 + NGAL + FABP + DDimer | 96.9 | 95.0 | 0.986 |
| 57. ICAM1 + NGAL + FABP + CRP | 96.9 | 95.0 | 0.986 |
| 58. ICAM1 + LSel + FABP + IL6 | 95.9 | 95.0 | 0.994 |
| 59. ICAM1 + LSel + FABP + NGAL | 99.0 | 96.7 | 0.996 |
| 60. ICAM1 + LSel + FABP + DDimer | 96.9 | 95.0 | 0.993 |
| 61. ICAM1 + LSel + FABP + CRP | 96.9 | 93.3 | 0.993 |
| 62. ICAM1 + LSel + FABP + sTNFRI | 96.9 | 93.3 | 0.993 |
| 63. ICAM1 + PSel + FABP + IL6 | 98.0 | 95.0 | 0.994 |
| 64. ICAM1 + PSel + FABP + NGAL | 96.9 | 96.7 | 0.996 |
| 65. ICAM1 + PSel + FABP + DDimer | 96.9 | 93.3 | 0.991 |
| 66. ICAM1 + PSel + FABP + CRP | 98.0 | 91.7 | 0.990 |
| 67. ICAM1 + PSel + FABP + sTNFRI | 96.9 | 93.3 | 0.990 |
| 68. ICAM1 + PSel + LSel + FABP | 100.0 | 95.0 | 0.997 |
| 69. VCAM1 + NGAL + FABP + DDimer | 96.9 | 93.3 | 0.988 |
| 70. VCAM1 + ICAM1 + LSel + FABP | 99.0 | 95.0 | 0.993 |
| 71. VCAM1 + LSel + FABP + DDimer | 92.9 | 95.0 | 0.971 |
| 72. VCAM1 + LSel + FABP + NGAL | 96.9 | 93.3 | 0.991 |
| 73. FABP + NGAL + sTNFRI | 95.9 | 93.3 | 0.986 |

Biomarker concentrations can be determined by contacting the sample with a substrate having probes specific for each of the biomarkers included in the combination of biomarkers. Interactions between a biomarker and its respective probe can be monitored and quantified using various techniques that are well-known in the art. Biomarker concentrations are preferably measured in ng/ml.

Preferably, a solid state device is used in the methods of the present invention, preferably the Biochip Array Technology system (BAT) (available from Randox Laboratories Limited). More preferably, the Evidence Evolution and Evidence Investigator apparatus (available from Randox Laboratories) may be used to determine the levels of biomarkers in the sample.

Control values are derived from the concentration of corresponding biomarkers in a biological sample obtained from an individual or individuals who have not undergone a stroke. Such individual(s) who have not undergone stroke may be, for example, healthy individuals, individuals suffering from diseases other than stroke. Alternatively, the control values may correspond to the concentration of each of the biomarker in a sample obtained from the patient prior to the stroke event.

For the avoidance of doubt, the term 'corresponding biomarkers' means that concentrations of the same combination of biomarkers that are determined in respect of the patient's sample are also used to determine the control values. For example, if the concentration of ICAM-1 and L-selectin in the patient's sample is determined, then the concentration of ICAM-1 and L-selectin in the control sample will also be determined.

In a preferred embodiment, each of the patient and control biomarker concentration values is inputted into one or more statistical algorithms to produce an output value that indicates whether a stroke has occurred.

The cut-off concentrations or values are derived using a statistical technique; various different methods are available for developing statistical algorithms and are well-known to those skilled in the art. A standard method of biomarker statistical analysis is to use univariate methods to compare biomarker levels in various groups and highlight those biomarkers whose concentrations significantly differ across and between particular groups.

The accuracy of statistical methods used in accordance with the present invention can be best described by their receiver operating characteristics (ROC). The ROC curve addresses both the sensitivity, the number of true positives, and the specificity, the number of true negatives, of the test. Therefore, sensitivity and specificity values for a given combination of biomarkers are an indication of the accuracy of the assay. For example, if a biomarker combination has sensitivity and specificity values of 80%, out of 100 patients which have stroke, 80 will be correctly identified from the determination of the presence of the particular combination of biomarkers as positive for stroke, while out of 100 patients who have not suffered a stroke 80 will accurately test negative for the disease.

If two or more biomarkers are to be used in the diagnostic method a suitable mathematical model, such as logistic regression equation, can be derived. The logistic regression equation might include other variables such as age and gender of patient. The ROC curve can be used to assess the accuracy of the logistic regression model. The logistic regression equation can be used independently or in an algorithm to aid clinical decision making Although a logistic regression equation is a common mathematical/statistical procedure used in such cases and is preferred in the context of the present invention, other mathematical/statistical procedures can also be used.

By way of example, a logistic regression equation applicable to the present invention (at a classification cut-off value of 0.5) for the biomarker combination ICAM-1, L-selectin, D-dimer and sTNFR1 for indication of stroke versus non-stroke (control) in a patient suspected of having had or currently experiencing a stroke is calculated as follows:

$$\text{Probability of Stroke} = \frac{1}{1 + e^{-(2.105 + 0.27[ICAM-1] - 0.018[L\text{-}selectin] + 0.071[D\text{-}dimer] + 8.945[sTNFRI])}}$$

where [ICAM-1], [L-selectin], [D-dimer] and [sTNFRI] are the concentrations of ICAM-1, L-selectin, D-dimer and sTNFRI measured in a blood sample taken from the patient (see number 118 of Table 1 for AUC value).

If the outcome of carrying out the method of the invention is a positive diagnosis of stoke, then the patient should be treated accordingly. However, since the most appropriate and efficacious treatment varies according to the stoke sub-type, it is useful to be able to further differentiate between the three different sub-types following a positive diagnosis of stroke. For example, if the patient has suffered an IS, thrombolytic therapy such as tissue plasminogen activator (TPA) can be administered to break-down clots. Alternatively, if the patient has suffered a TIA, blood thinners such as warfarin and aspirin may be prescribed.

Therefore, according to a further embodiment, the method according to the first aspect of the invention may optionally include carrying out additional steps for differentially diagnosing between IS and TIA as defined in the fourth aspect of this invention.

A second related aspect of the invention provides a substrate comprising probes for at least two biomarkers selected from ICAM-1, L-selectin, P-selectin, VCAM-1, IL-6, sTNFR1, D-dimer and CRP for use in a method for diagnosing stroke in a patient according to the first aspect of the invention, wherein the substrate comprises a probe for at least one of ICAM-1, L-selectin, P-selectin and VCAM-1. Optionally, the substrate may further comprise a probe for h-FABP.

Preferably the substrate has at least two probes immobilised thereon, more preferably three, four or more probes, wherein each probe is specific to an individual biomarker. As used herein, the term 'specific' means that the probe binds only to one of the biomarkers of the invention, with negligible binding to other biomarkers of the invention or to other analytes in the biological sample being analysed. This ensures that the integrity of the diagnostic assay and its result using the biomarkers of the invention is not compromised by additional binding events.

The substrate can be any substance able to support one or more probes, but is preferably a biochip. A biochip is a planar substrate that may be, for example, mineral or polymer based, but is preferably ceramic. When identifying the various biomarkers/proteins of the invention it will be apparent to the skilled person that as well as identifying the full length protein, the identification of a fragment or several fragments of a protein is possible, provided this allows accurate identification of the protein. Similarly, although a preferred probe of the invention is a polyclonal or monoclonal antibody, other probes such as aptamers, molecular imprinted polymers, phages, short chain antibody fragments and other antibody-based probes may be used.

In a related third aspect of the invention, a substrate according to the second aspect is used in the method according to the first aspect of the invention.

The present invention also provides kits comprising probes for at least two biomarkers selected from ICAM-1, L-selectin, P-selectin, VCAM-1, IL-6, sTNFR1, D-dimer and CRP, additional reagents, substrate/reaction surfaces and/or instructions for use. Such kits can be used to diagnose stroke in a patient a according to the first aspect of the invention.

A fourth aspect of the present invention provides a method of aiding the diagnosis of ischaemic stroke in a patient suspected of having a stroke, comprising
 i) determining the concentration of VCAM-1 and one or more biomarkers selected from h-FABP, IL-6 and CRP in an in vitro sample obtained from the patient; and
 ii) establishing the significance of the concentration of the biomarkers by comparing the concentration value for each biomarker with a corresponding control value, wherein the corresponding control value is the concentration value for the corresponding biomarker determined from an in vitro sample obtained from a transient ischaemic attack patient or patients.

Advantageously, this method can be used to differentially diagnose between ischemic stroke and a transient ischaemic attack.

Each of the biomarkers or biomarker combinations can be used alone or as complementary biomarkers. Preferred biomarker combinations can be identified from the data in Table 4.

The control values can be established by measuring the concentration of the biomarkers VCAM-1 and one or more h-FABP, IL-6 and CRP in one or more patients clinically diagnosed as having, or having had, a TIA. The diagnosis may be derived using techniques such as clinician examination and neuroimaging analysis (which would rule out the possibility of HS).

Biomarker concentrations can be determined by contacting the sample with a substrate having probes specific for each of the biomarkers included in the combination of biomarkers. Interactions between biomarker and its respective probe can be monitored and quantified using various techniques that are well-known in the art.

In a preferred embodiment, each of the patient and control biomarker concentration values is inputted into one or more statistical algorithms to produce an output value that indicates whether ischemic stroke has occurred.

By way of example, the following concentrations ('cut-off' concentration) support the diagnosis of IS in the patient: h-FABP about 10 ng/ml; VCAM-1.gtoreq.about 570 ng/ml; CRP.gtoreq.about 30 .mu.g/ml; and IL-6.gtoreq.about 12 .mu.g/ml. However, biomarker normal or 'background' concentrations may exhibit slight variation due to, for example, age, gender or ethnic/geographical genotypes. As a result, the cut-off value used may also slightly vary due to optimisation depending upon the target patient/population.

The cut-off concentrations or values are usually derived using statistical techniques. A standard method of biomarker statistical analysis is to use univariate methods to compare biomarker levels in various groups and highlight those biomarkers whose concentrations significantly differ between particular groups. This is followed by Receiver Operator Characteristic (ROC) analysis.

As described above in relation to the first aspect of the invention, a ROC curve is a preferred method of assessing the accuracy of a diagnostic test. It also provides a measure of the predictive power of the test in the form of the area under the curve (AUC), which can have values of 0.5 to 1.0. As a general rule, a test with a sensitivity of about 80% or more and a specificity of about 80% or more is regarded in the art as a test of potential use, although these values vary according to the clinical application.

For discriminating between IS and TIA according to the method of the invention, a high specificity is crucial. For a given test, the closer the value of its AUC is to 1.0, the greater its predictive power. A logistic regression equation can be derived for any test involving two or more biomarkers. The logistic regression equation may include other variables, such as the age and gender of the patient. The ROC curve can be used to assess the accuracy of the logistic regression model. The logistic regression equation can be used independently or in an algorithm to aid clinical decision making. Although a logistic regression equation is a common mathematical/statistical tool, other mathematical/statistical procedures are well known in the art and can be used in accordance with the present invention.

The outcome of carrying out the method according to this aspect of the invention will be a diagnosis of either IS or TIA and the patient should then be treated accordingly. If as a result of carrying out the method of the invention it is determined that the patient has suffered an IS, appropriate treatment such as thrombolytic therapy (e.g. tissue plasminogen activator (TPA)) can be administered to break-down clots. This may be administered in conjunction with other appropriate therapies, as determined by a physician. If as a result of carrying out the method of the invention it is determined that the patient has suffered a TIA, blood thinners such as warfarin and aspirin may be prescribed and administered.

A related fifth aspect of the invention provides a substrate comprising probes for VCAM-1 and at least one other biomarker selected from h-FABP, IL-6 and CRP for use in a method for aiding the diagnosis of ischaemic stroke in a patient according to the present invention.

The substrate comprises at least two, preferably three or four probes, each probe specific to an individual biomarker. As used herein, the term 'specific' means that the probe binds only to one of the biomarkers of the invention, with negligible binding to other biomarkers of the invention or to other analytes in the biological sample being analysed. This ensures that the integrity of the diagnostic assay and its result using the biomarkers of the invention is not compromised by additional binding events.

The substrate can be any substance able to support one or more probes, but is preferably a biochip. A biochip is a planar substrate that may be, for example, mineral or polymer based, but is preferably ceramic. When identifying the various biomarkers/proteins of the invention it will be apparent to the skilled person that as well as identifying the full length protein, the identification of a fragment or several fragments of a protein is possible, provided this allows accurate identification of the protein. Similarly, although a preferred probe of the invention is a polyclonal or monoclonal antibody, other probes such as aptamers, molecular imprinted polymers, phages, short chain antibody fragments and other antibody-based probes may be used.

Preferably, a solid state device is used in the methods of the present invention, preferably the Biochip Array Technology system (BAT) (available from Randox Laboratories Limited). More preferably, the Evidence Evolution and Evidence Investigator apparatus (available from Randox Laboratories) may be used to determine the levels of biomarkers in the sample.

In a related sixth aspect of the invention, a substrate according to the fifth aspect is used in the method according to the fourth aspect of the invention.

The invention also provides kits comprising probes for VCAM-1 and at least one other biomarker selected from h-FABP, IL-6 and CRP, additional reagents, substrate/reaction surfaces and/or instructions for use. Such kits can be used to diagnose IS in a patient according to the third aspect of the invention.

A further aspect of the invention is directed to the use of one or more of h-FABP, sTNFR1, IL-6, D-dimer, L-selectin, P-selectin, ICAM-1, VCAM-1 and CRP as complementary biomarkers of stroke or stroke sub-type. As complementary biomarkers they may be used for stroke/stroke sub-type diagnosis in conjunction with proteins such as DJ-1, BNP, S100 .beta., MMP-9, MCP-1, ApoC1, ApoC3, von Willebrand factor, NMDA receptors, ADMA and Lp-PLA2.

The invention will now be described further by reference to the following non-limiting example.

EXAMPLE

Patient Group

The study consisted of 98 patients displaying stroke symptoms admitted to the Emergency Department of KAT General Hospital, Athens, Greece. Blood samples were taken at the time of admission and at days 1, 2, 3 and 7. The mean time from the onset of stroke symptoms and hospital admission was 3.2 hours. The mean age of the patients was 75.2 years (standard deviation 9.4). Clinician evaluation (using criteria highlighted in the Background section) and neuroimaging techniques identified 44 ischaemic stroke (IS), 25 haemorrhagic stroke (HS), 29 transient ischaemic attack (TIA); 60 healthy subjects served as controls (C).

Sample Analysis

The following proteins were tested against EDTA plasma samples of blood obtained from the patients of the study group: ICAM-1, VCAM-1, E-selectin, L-selectin, P-selectin, IL-6, h-FABP, CRP, D-dimer, sTNFR1, TM and NGAL. The proteins were detected and quantified using multiplexed biochips incorporating biomarker-specific antibodies and the Evidence Investigator (Randox Laboratories Ltd, Crumlin, UK). The simultaneous immunoassays were performed according to manufacturer's instructions. A nine-point calibration curve and three reference controls were assayed for each biomarker to allow validation of results. For CRP IS vs TIA analysis, samples were diluted tenfold.

Statistical Analysis

Figure 2:
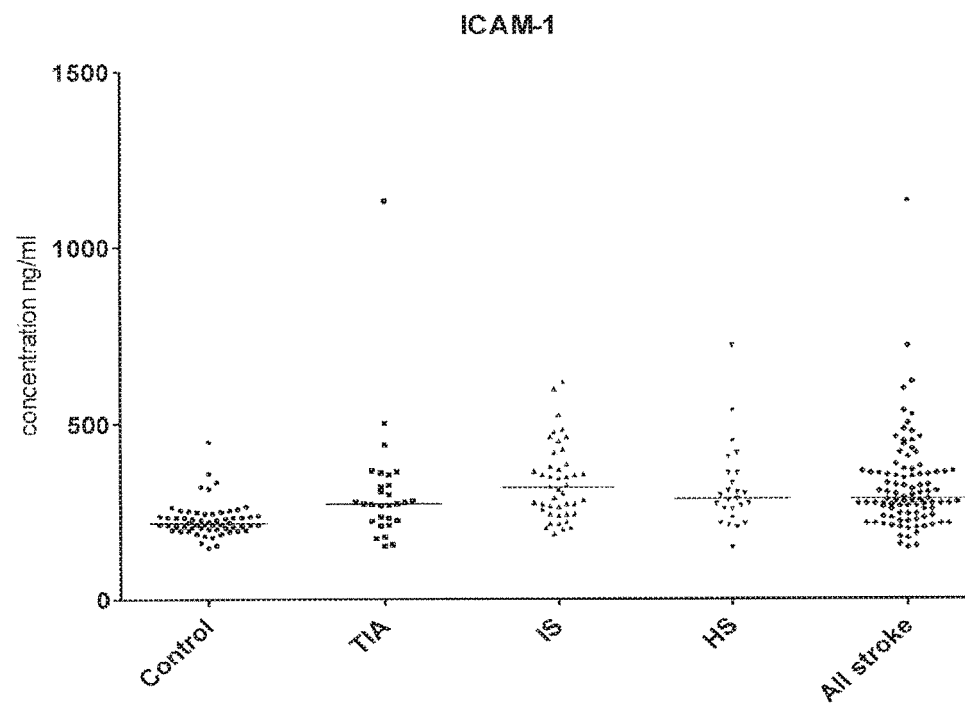
FIG. 2 is a graph showing the concentration of ICAM-1 for all stroke patients, each stroke sub-type and the control subjects.
Figure 3:
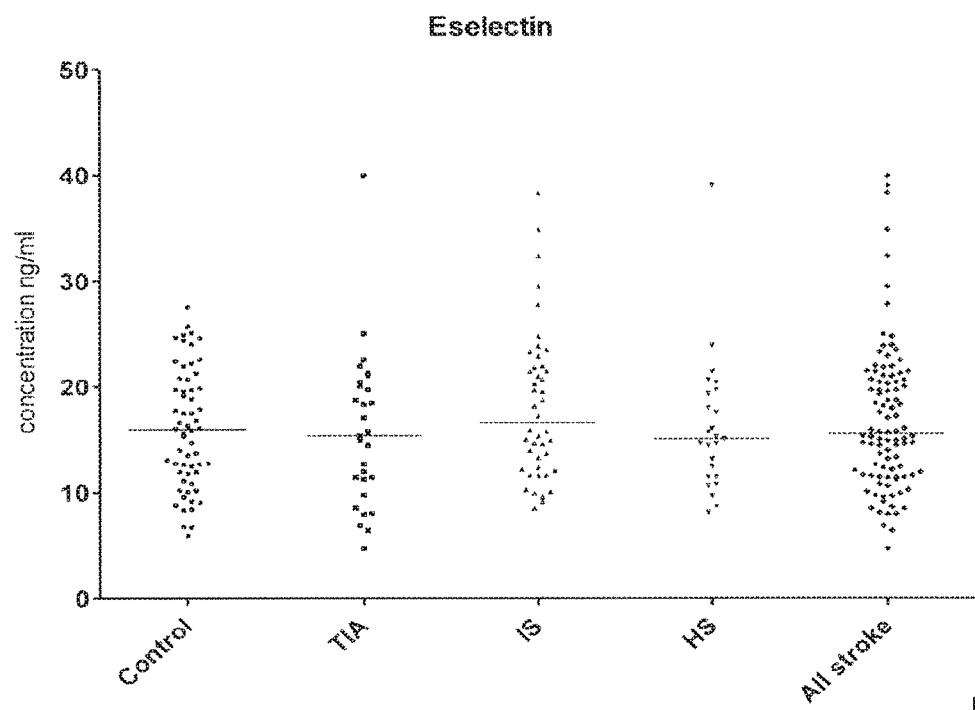
FIG. 3 is a graph showing the concentration of E-selectin for all stroke patients, each stroke sub-type and the control subjects.
Figure 4:
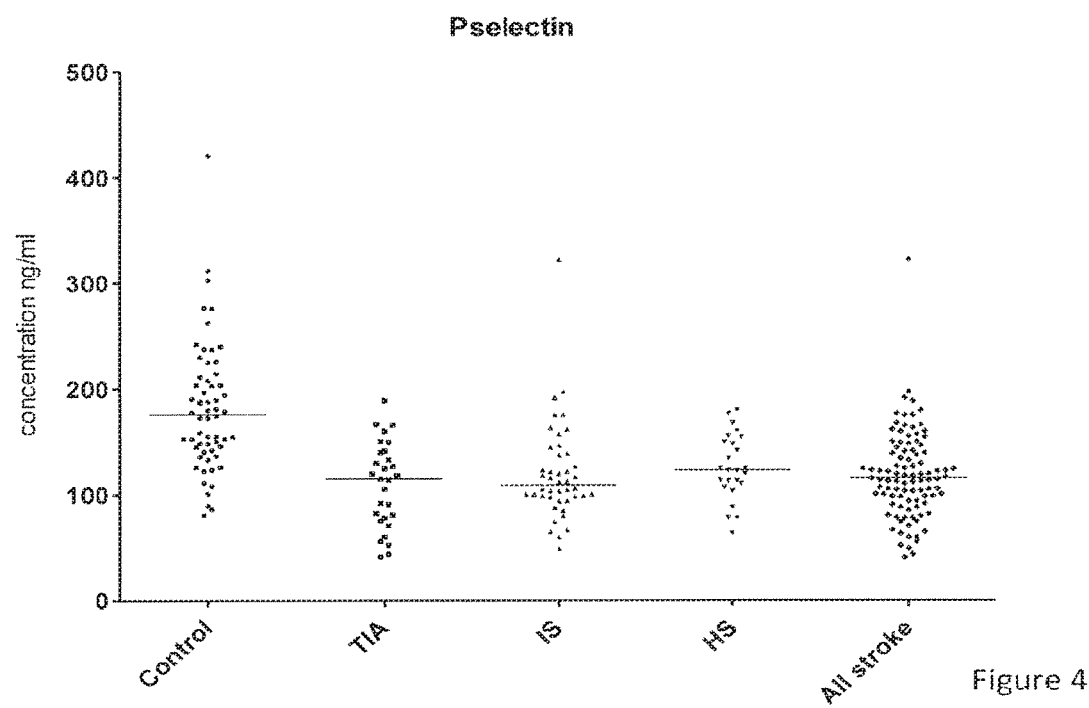
FIG. 4 is a graph showing the concentration of P-selectin for all stroke patients, each stroke sub-type and the control subjects.
Figure 5:
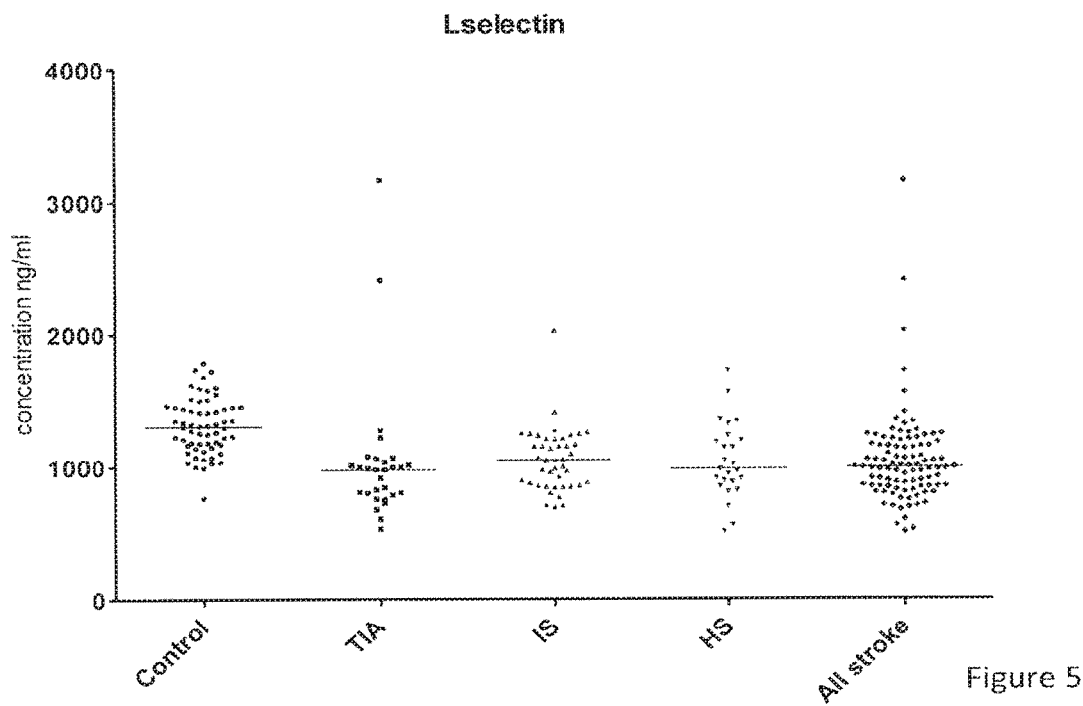
FIG. 5 is a graph showing the concentration of L-selectin for all stroke patients, each stroke sub-type and the control subjects.
Figure 6:
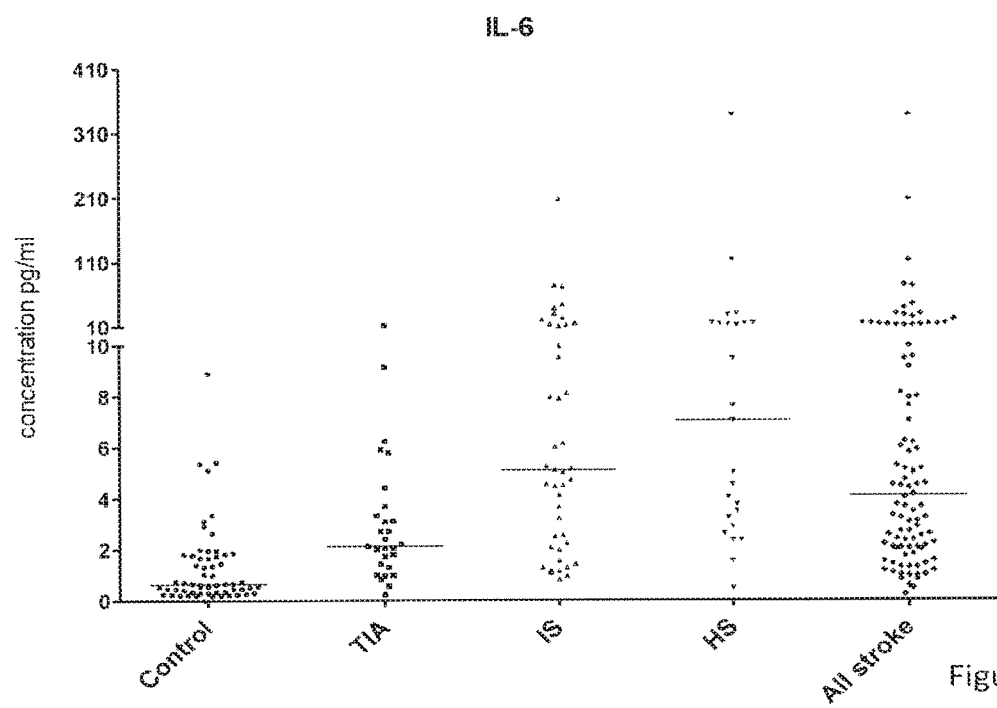
FIG. 6 is a graph showing the concentration of IL-6 for all stroke patients, each stroke sub-type and the control subjects.
Figure 7:
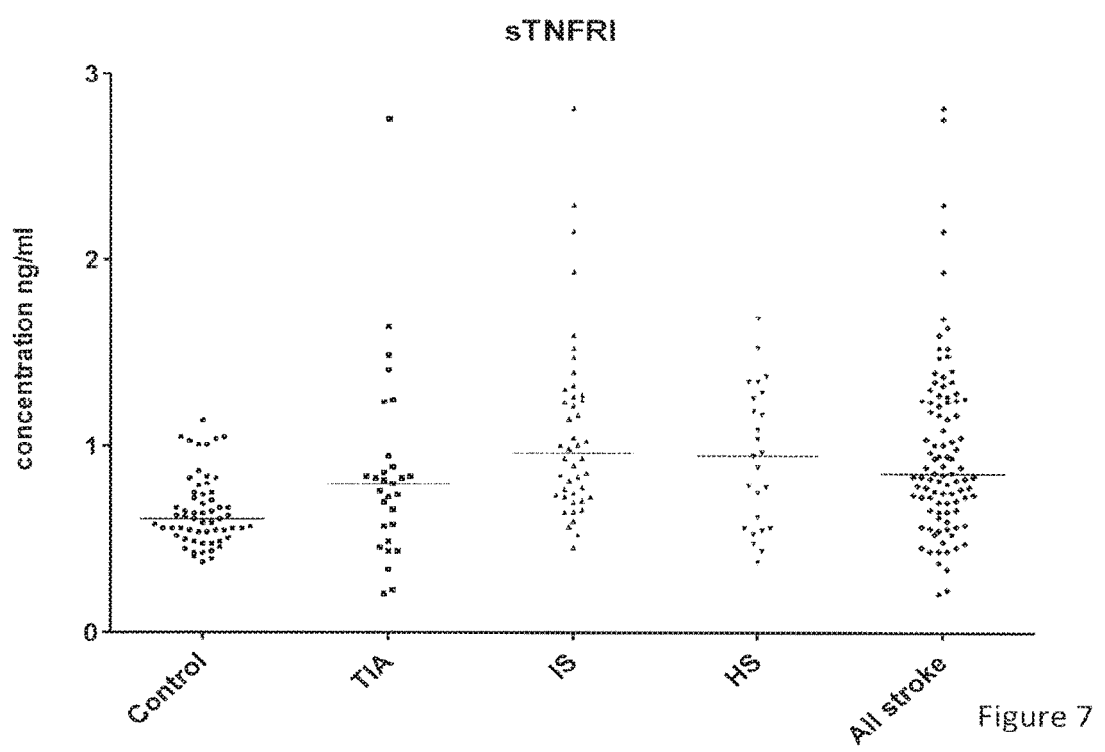
FIG. 7 is a graph showing the concentration of sTNFR1 for all stroke patients, each stroke sub-type and the control subjects.
Figure 8:
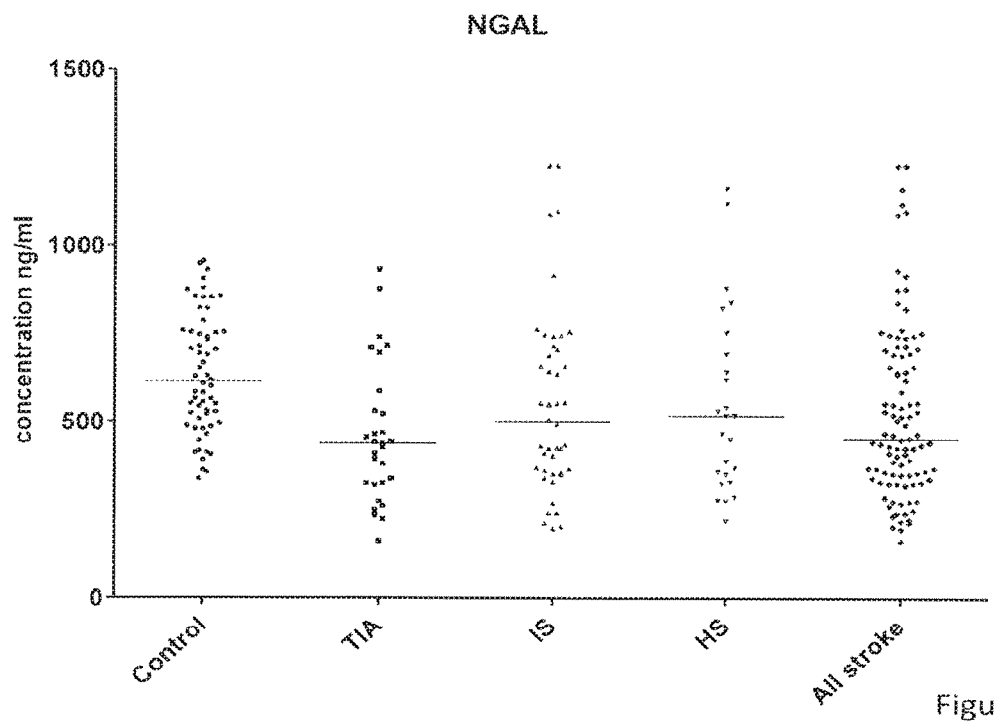
FIG. 8 is a graph showing the concentration of NGAL for all stroke patients, each stroke sub-type and the control subjects.
Figure 9:
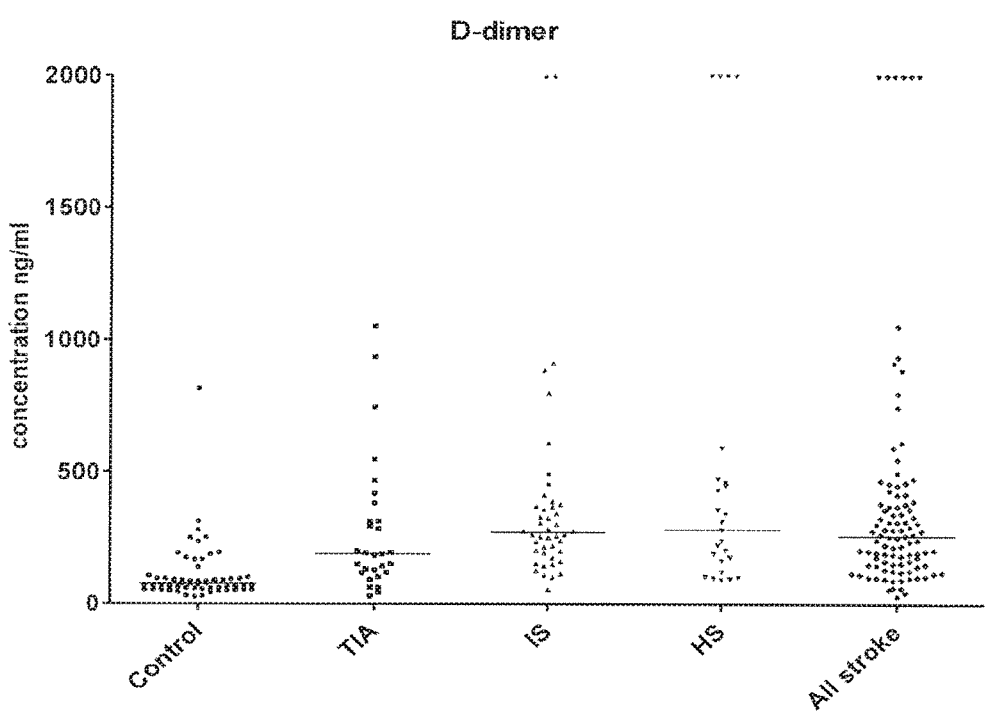
FIG. 9 is a graph showing the concentration of D-dimer for all stroke patients, each stroke sub-type and the control subjects.
Figure 10:
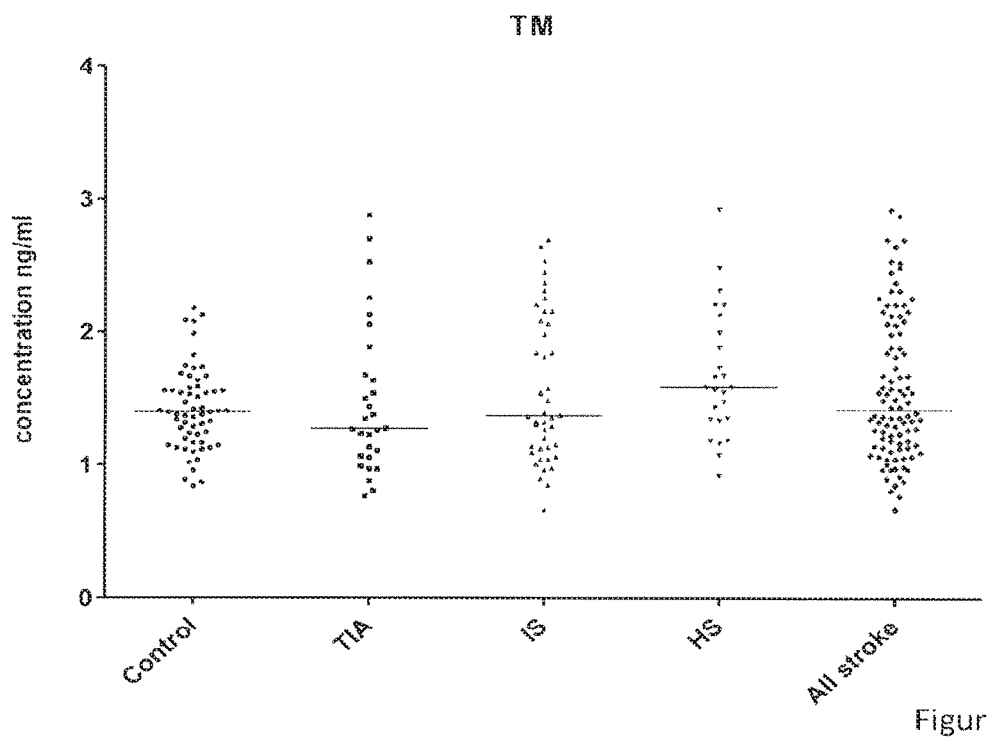
FIG. 10 is a graph showing the concentration of TM for all stroke patients, each stroke sub-type and the control subjects.
Figure 11:
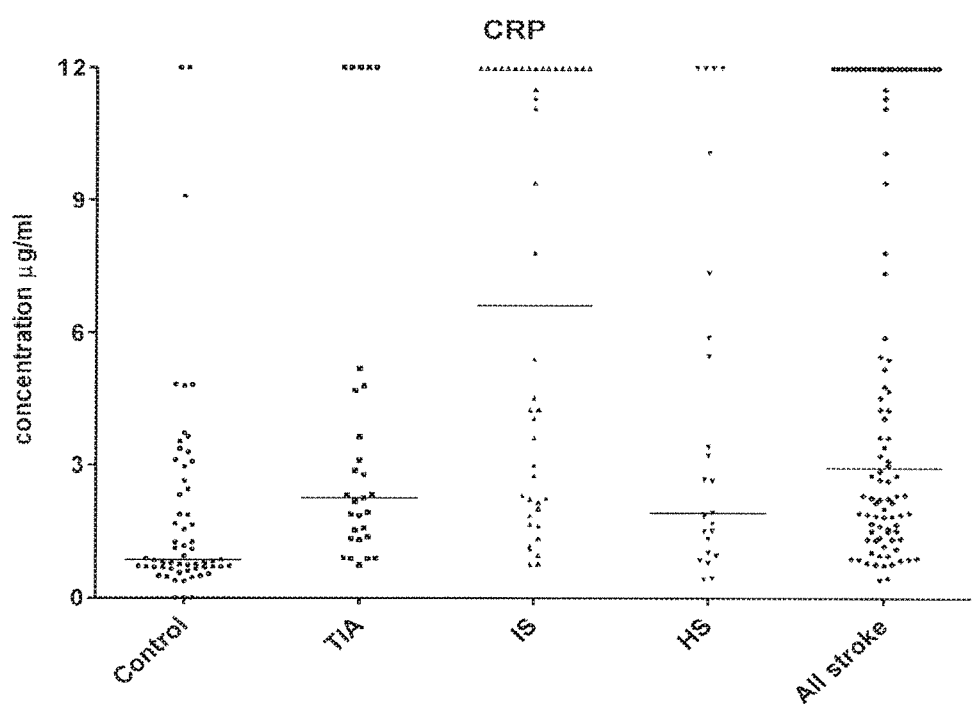
FIG. 11 is a graph showing the concentration of CRP for all stroke patients, each stroke sub-type and the control subjects.
Figure 12:
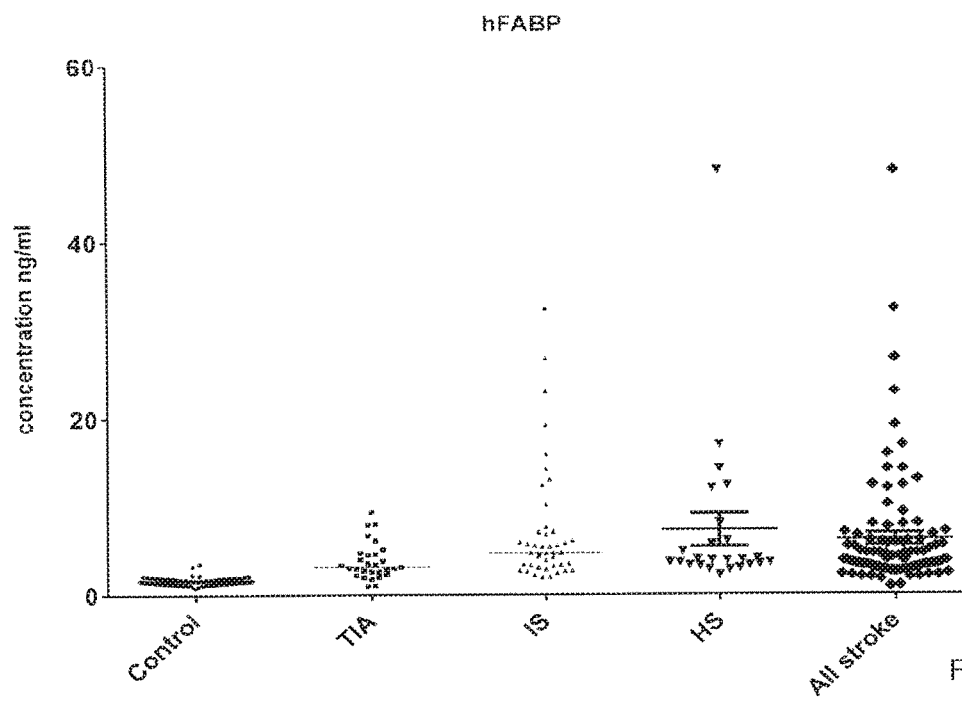
FIG. 12 is a graph showing the concentration of h-FABP for all stroke patients, each stroke sub-type and the control subjects.
Figure 13:
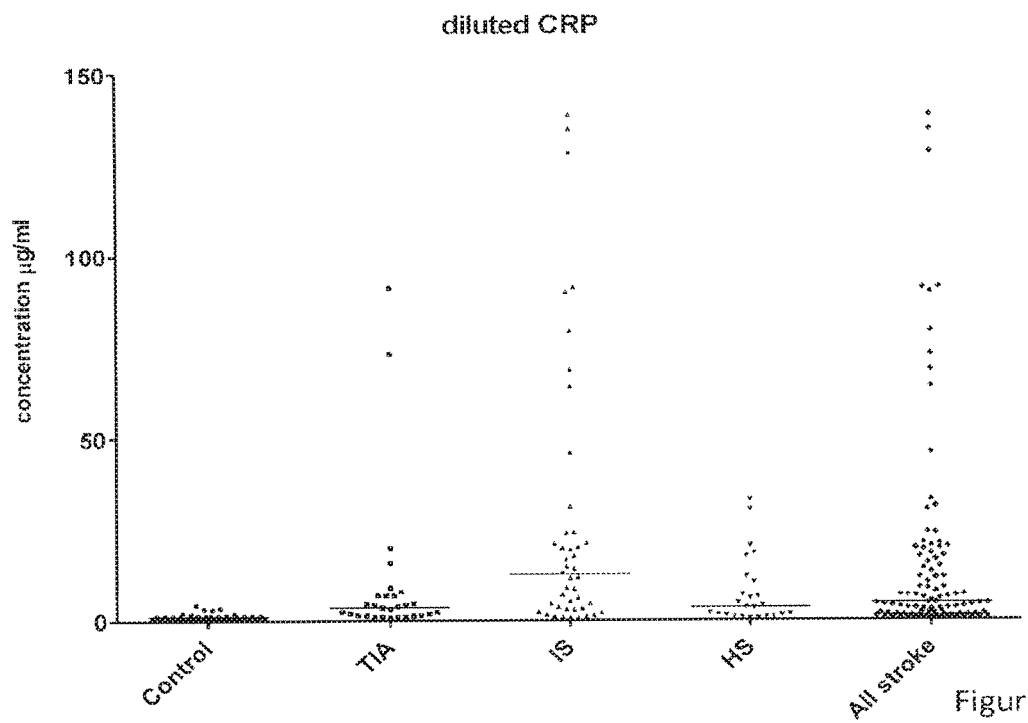
FIG. 13 is a graph showing the concentration of diluted CRP for all stroke patients, each stroke sub-type and the control subjects.

The Kruskal-Wallis test (significance limit 0.05) was used to identify analytes that were differentially expressed across the four groups (IS, HS, TIA and C). Post-hoc comparisons between the different groups were carried out using the Holm's sequential Bonferroni adjustment. Mann-Whitney test was used to compare 'All Stroke' and 'Control'. The results are shown in FIGS. 1-13.

Figure 14:
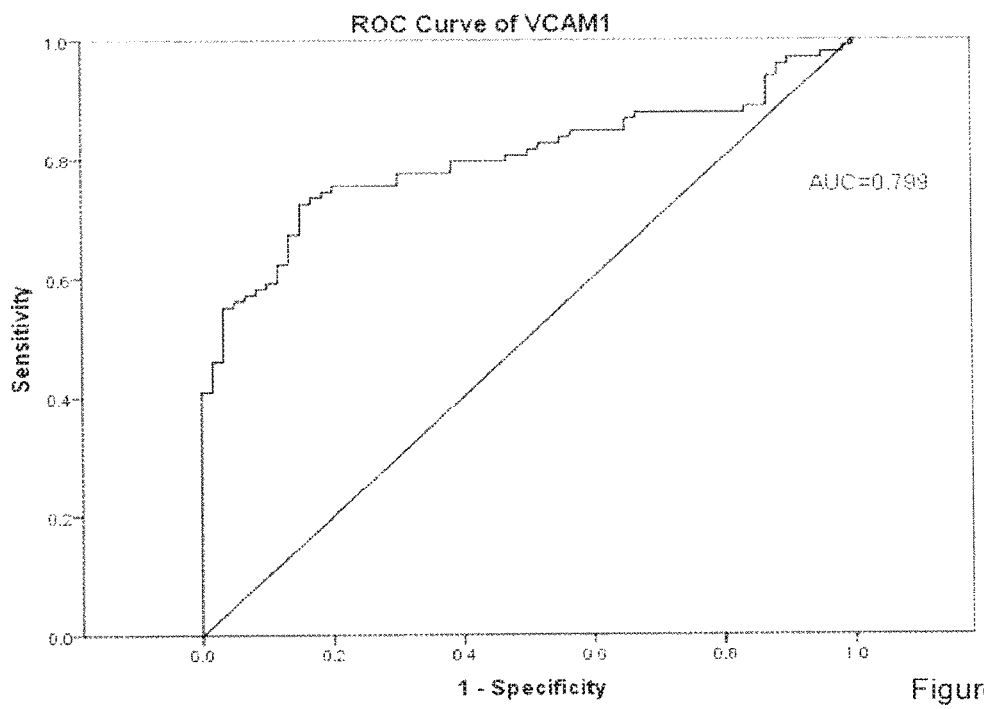
FIG. 14 is a ROC curve for VCAM-1 (all stroke v control)
Figure 15:
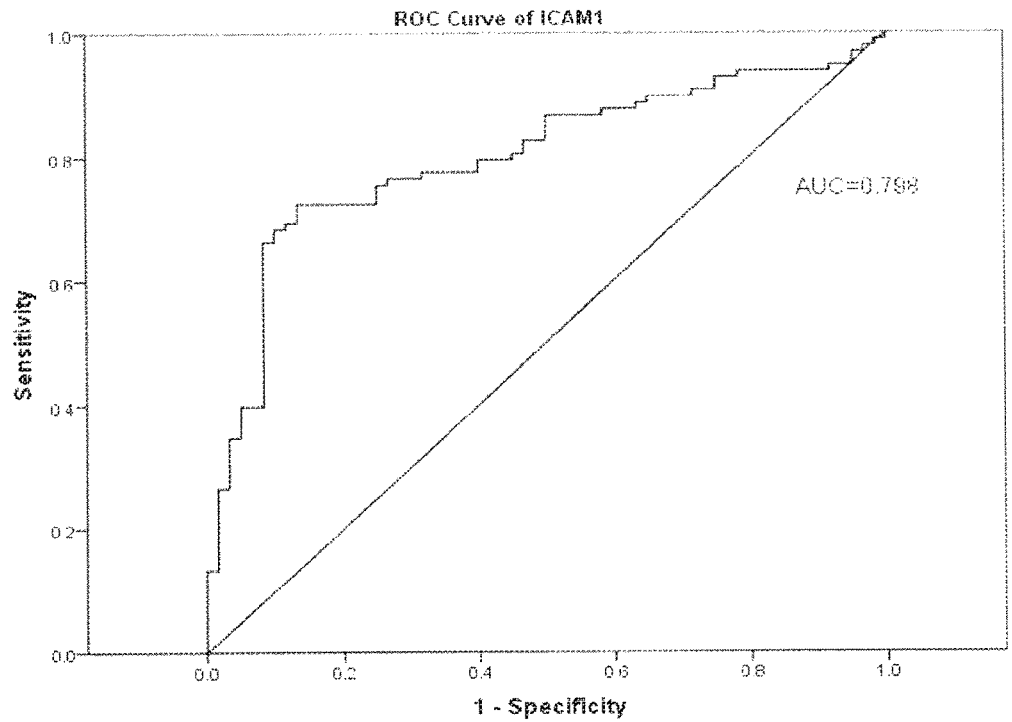
FIG. 15 is a ROC curve for ICAM-1 (all stroke v control)
Figure 16:
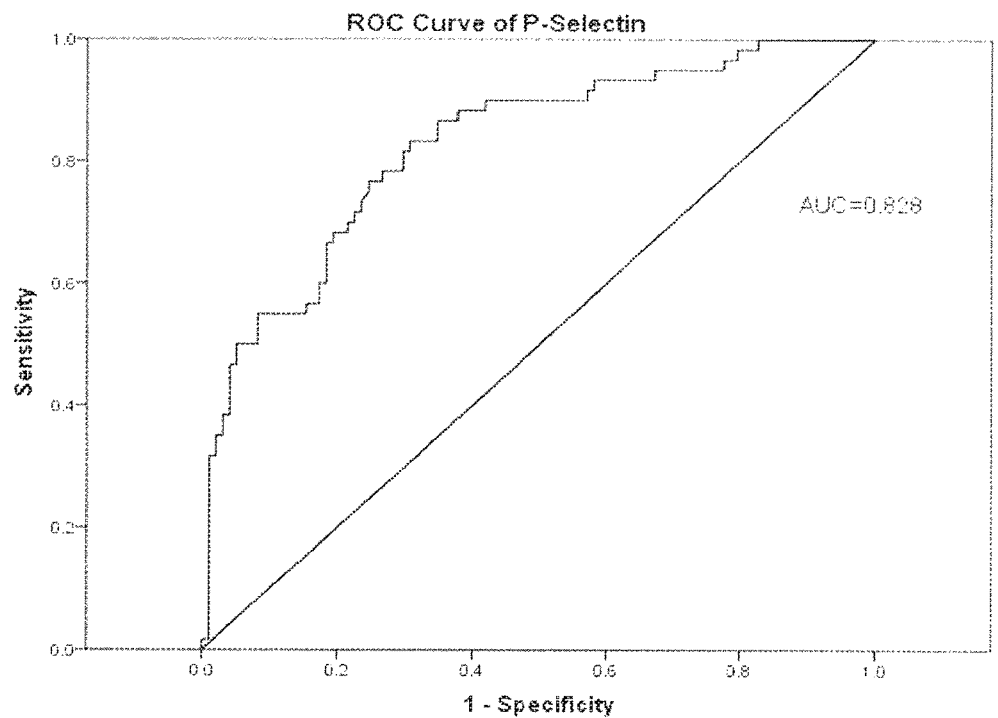
FIG. 16 is a ROC curve for P-selectin (all stroke v control)
Figure 17:
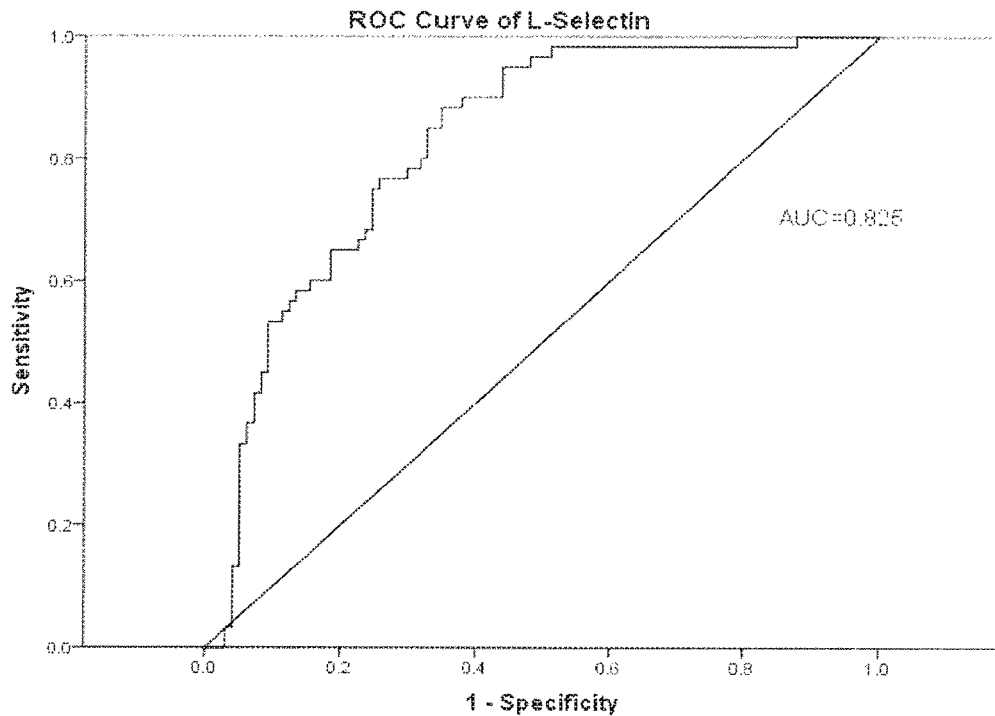
FIG. 17 is a ROC curve for L-selectin (all stroke v control)
Figure 18:
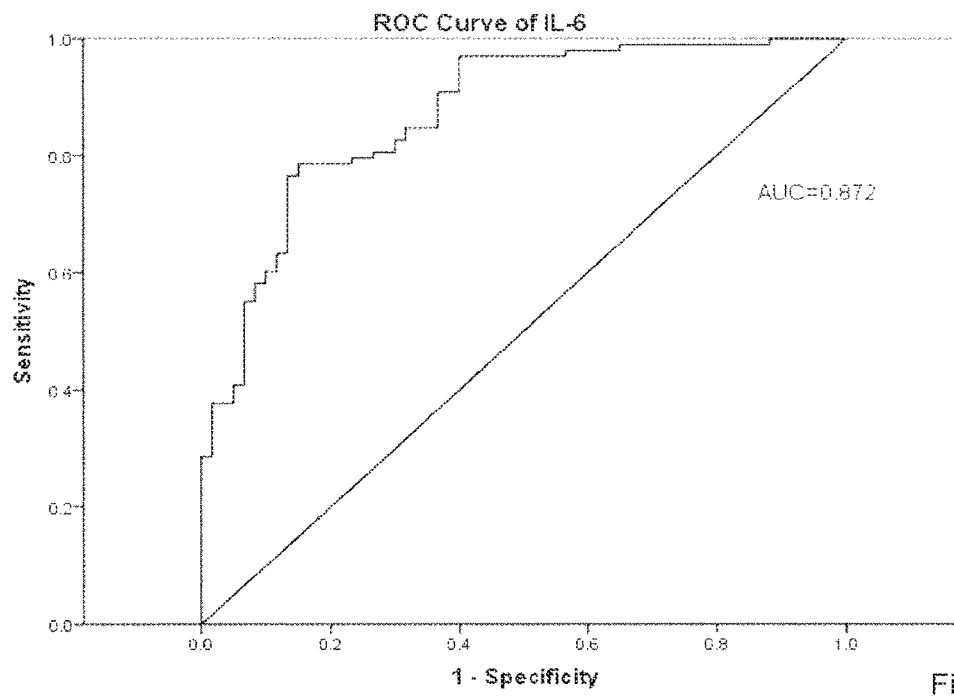
FIG. 18 is a ROC curve for IL-6 (all stroke v control)
Figure 19:
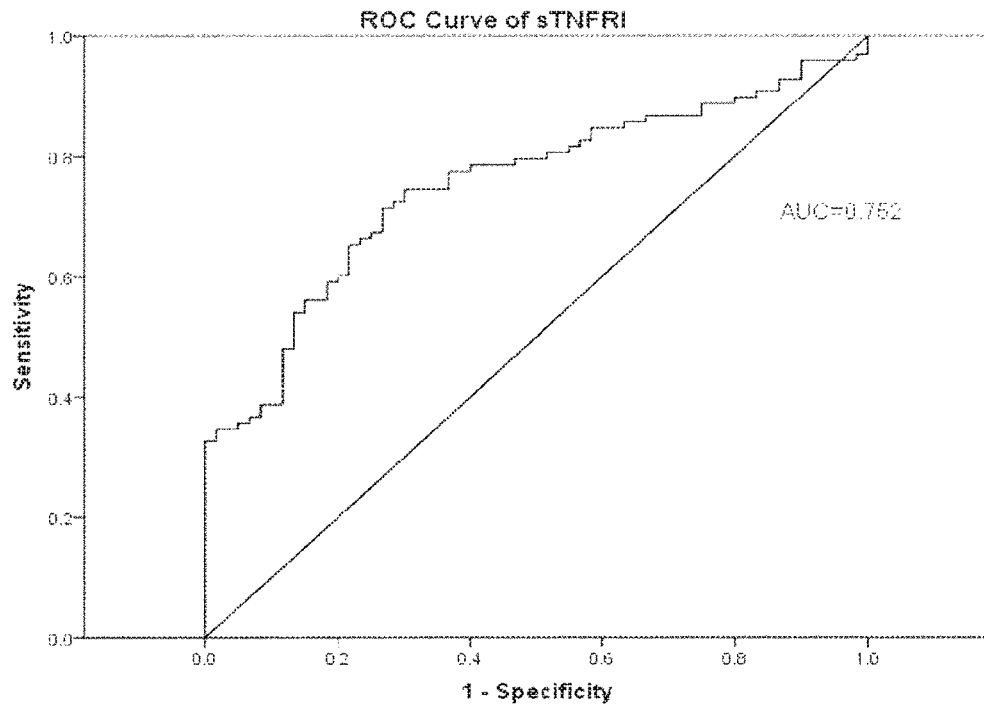
FIG. 19 is a ROC curve for sTNFR1 (all stroke v control)
Figure 20:
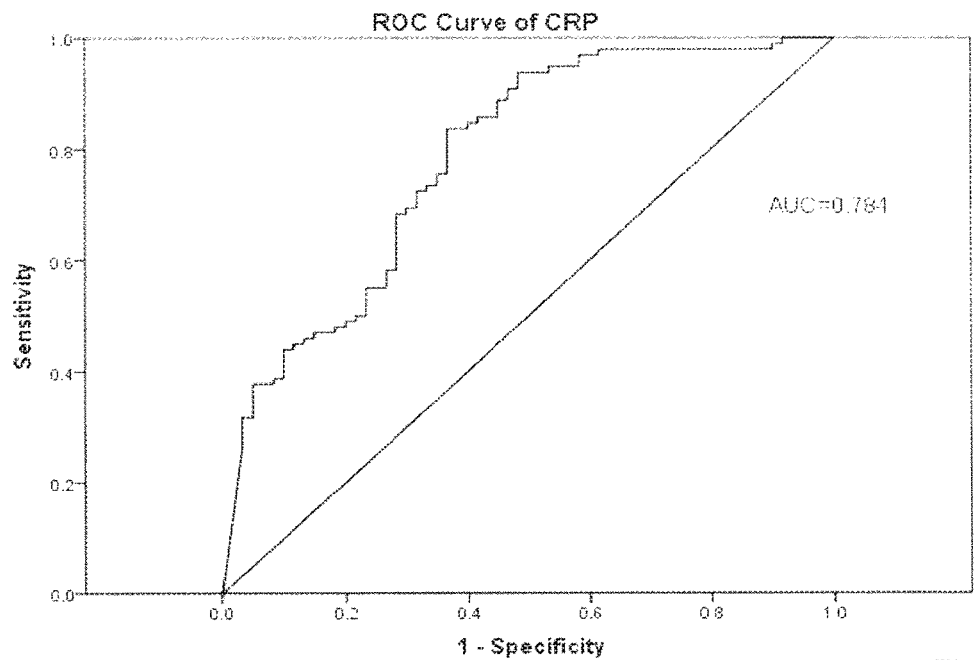
FIG. 20 is a ROC curve for CRP (all stroke v control)
Figure 21:
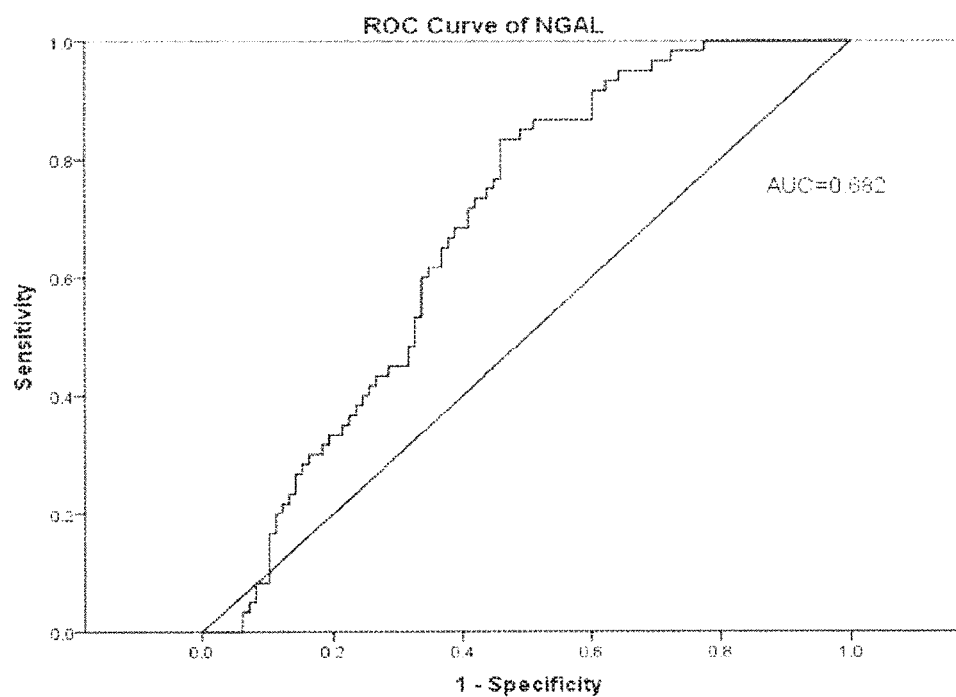
FIG. 21 is a ROC curve for NGAL (all stroke v control)
Figure 22:
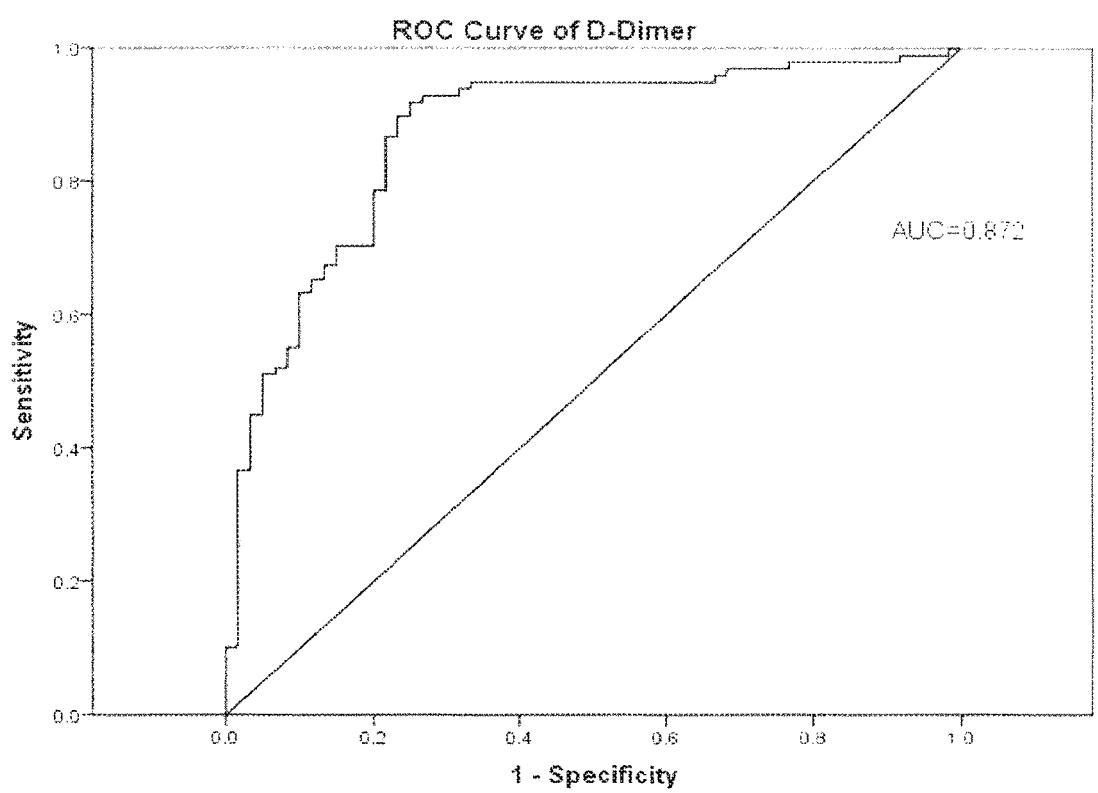
FIG. 22 is a ROC curve for D-dimer (all stroke v control).

Single biomarkers were subject to ROC curve analysis to assess sensitivity and specificity. Logistic regression was used to model the dependency of stroke and stroke subtype upon the concentration of various combinations of biomarkers followed by ROC curve analysis to assess the model's classification accuracy. The results are shown in FIGS. 1-22.

Results

Tables 1 and 2 detail the sensitivity, specificity and statistical power (AUC) of exemplary combinations of biomarkers for diagnosing stroke (all stroke v control). By combining two or more biomarkers selected from ICAM-1, VCAM-1, L-selectin, P-selectin, IL-6, CRP, D-dimer and sTNFR1 for testing the occurrence of stroke, a test with high diagnostic performance is achieved. Also, it has been found for the first time that the blood concentration of the proteins VCAM-1, IL-6, h-FABP and CRP are able to discriminate between IS and TIA. Critical to the usefulness of the invention is the high discriminatory power of the biomarker(s). A test which aims to discriminate IS from TIA, must have a high specificity as possible so as to rule out TIA.

If TIA cannot be ruled out by the biomarker(s), then the diagnosis will be of either an IS or TIA i.e. it will not be able to discriminate between these two stroke subtypes. Therefore, the specificity of the test should be as close to 100% as possible. The sensitivity of the test should be of sufficient magnitude to be of value to the patient and be economically viable. Table 3 shows the statistical analysis of analyte concentrations in patients who suffered TIA, IS and HS using Mann-Whitney and Kruskal-Wallis tests. Table 4 shows the ROC curve analysis (sensitivity and specificity values) of individual and grouped biomarkers for IS vs TIA. As can be seen, each of the biomarkers has 100% specificity and equal or greater sensitivity than the commonly used CAT scan. This facilitates clinical diagnosis and informs subsequent treatment decisions of suspected stroke patients in an economical and expeditious manner.

TABLE 3

| Analyte | IS v TIA | TOA v C | IS vC | HS v C | HS v IS | All v C |
|---|---|---|---|---|---|---|
| VCAM-1 | $P < 0.0001$ | ns | $P < 0.001$ | $P < 0.001$ | ns | $P < 0.0001$ |
| ICAM-1 | ns | $P < 0.01$ | $P < 0.001$ | $P < 0.001$ | ns | $P < 0.0001$ |
| E-selectin | ns | ns | ns | ns | ns | ns |
| L-selectin | ns | $P < 0.001$ | $P < 0.001$ | $P < 0.001$ | ns | $P < 0.0001$ |
| P-selectin | ns | $P < 0.001$ | $P < 0.001$ | $P < 0.001$ | ns | $P < 0.001$ |
| IL-6 | $P < 0.01$ | $P < 0.001$ | $P < 0.001$ | $P < 0.001$ | ns | $P < 0.001$ |
| h-FABP | $P < 0.01$ | $P < 0.001$ | $P < 0.001$ | $P < 0.001$ | ns | $P < 0.001$ |
| CRP | $P < 0.05$ | $P < 0.001$ | $P < 0.001$ | $P < 0.001$ | $P < 0.05$ | $P < 0.001$ |
| D-dimer | $P < 0.05$ | $P < 0.001$ | $P < 0.001$ | $P < 0.01$ | ns | $P < 0.001$ |
| NGAL | ns | ns | ns | ns | ns | ns |
| sTNFR1 | $P < 0.05$ | $P < 0.001$ | $P < 0.001$ | $P < 0.001$ | ns | $P < 0.001$ |
| TM | ns | ns | ns | ns | ns | ns |

[All stroke = TIA + IS + HS; C = control; ns = not significantly different at the 5% level ($P > 0.05$)]

TABLE 4

| | Ischemic Stroke (IS) | | |
|---|---|---|---|
| Biomarker(s) | AUC | % Sensitivity | % Specificity |
| VCAM-1 | 0.755 | 24.88 | 100 |
| IL-6 | 0.727 | 23.26 | 100 |
| h-FABP | 0.700 | 20.45 | 100 |
| VCAM-1 + IL-6 | 0.801 | 30.23 | 100 |
| VCAM-1 + IL-6 + CRP | 0.818 | 34.88 | 100 |
| VCAM-1 + CRP | 0.793 | 34.09 | 100 |
| VCAM-1 + h-FABP | 0.811 | 31.82 | 100 |
| VCAM-1 + h-FABP + IL-6 | 0.812 | 31.82 | 100 |
| VCAM-1 + h-FABP + CRP | 0.816 | 34.09 | 100 |
| VCAM-1 + h-FABP + IL-6 + CRP | 0.820 | 34.09 | 100 |

Clinical Use of the Invention

Use of the invention can be envisaged in the following scenarios relating to an individual who suffers a stroke-like event:

i) in transit to the hospital a biological fluid sample is taken from the individual and tested for all stroke types using biomarkers of the invention—a positive stroke result is confirmed and further stratified into HS or IS/TIA following examination of the individual by a clinician and analysis using a CAT scan. If HS is ruled out, a further biomarker test is implemented to delineate IS/TIA. ii) at the hospital examination by a clinician is preceded by stroke biomarker analysis of a biological fluid sample taken from the individual in association with a CAT scan examination—if HS is ruled out, a further biomarker test is implemented to delineate IS/TIA.

Abbreviations

IL-6—interleukin-6 ICAM-1—intracellular adhesion molecule-1 VCAM-1—vascular cell adhesion molecule-1 CRP—C-reactive protein h-FABP—human fatty acid binding protein sTNFR—soluble TNF.alpha. receptor TM—thrombomodulin NGAL—neutrophil-associated gelatinase lipocalin MMP-9—matrix metalloproteinase-9 BNP—brain natriuretic peptide ADMA—asymmetric dimethylarginine Lp-PLA2—lipoprotein-associated phospholipase A2

The invention claimed is:

1. A method for diagnosing stroke in a patient suspected of having a stroke, comprising determining the concentration of at least two biomarkers in an in vitro sample obtained from the patient and establishing the significance of the concentration of the biomarkers by comparing the concentration value for each biomarker with a corresponding control value, wherein the at least two biomarkers are selected from ICAM-1 (intracellular adhesion molecule 1), L-selectin, P-selectin, VCAM-1 (vascular cell adhesion molecule 1), IL-6 (interleukin-6), sTNFR1 (soluble tumour necrosis factor receptor 1), D-dimer and CRP (C-reactive protein), and wherein at least one of the two biomarkers is selected from ICAM-1, L-selectin, P-selectin and VCAM-1, wherein if stoke is diagnosed, a second method is carried out in order to differentially diagnose the stroke type, the second method comprising:
  i) determining the concentration of VCAM-1 and one or more biomarkers selected from h-FABP (human fatty acid binding protein), IL-6 and CRP in an in vitro sample obtained from the patient; and
  ii) establishing the significance of the concentration of the biomarkers by comparing the concentration value for each biomarker with a corresponding control value, wherein the corresponding control value is the concentration value for the corresponding biomarker determined from an in vitro sample obtained from a transient ischaemic attack patient or patients.

* * * * *